US012653820B2

(12) United States Patent
Puster et al.

(10) Patent No.: US 12,653,820 B2
(45) Date of Patent: Jun. 16, 2026

(54) HYDROMORPHONE FORMULATIONS FOR MULTI-DOSE PRODUCTS

(71) Applicant: Hikma Pharmaceuticals USA Inc., Berkeley Heights, NJ (US)

(72) Inventors: Nathan Puster, Bedford, OH (US); Rand H. Ahmad, Bedford, OH (US); Gyongyi Szakalas-Gratzl, Bedford, OH (US); Ragheb M. AbuRmaileh, Bedford, OH (US)

(73) Assignee: Hikma Pharmaceuticals USA Inc., Berkeley Heights (CA)

( * ) Notice: Subject to any disclaimer, the term of this patent is extended or adjusted under 35 U.S.C. 154(b) by 0 days.

(21) Appl. No.: 18/152,303

(22) Filed: Jan. 10, 2023

(65) Prior Publication Data

US 2024/0238275 A1 Jul. 18, 2024

(51) Int. Cl.

| | |
|---|---|
| ***A61K 31/485*** | (2006.01) |
| ***A61K 9/08*** | (2006.01) |
| ***A61K 47/14*** | (2017.01) |
| ***A61K 47/18*** | (2017.01) |

(52) U.S. Cl.

CPC .............. *A61K 31/485* (2013.01); *A61K 9/08* (2013.01); *A61K 47/14* (2013.01); *A61K 47/183* (2013.01)

(58) Field of Classification Search

None

See application file for complete search history.

(56) References Cited

U.S. PATENT DOCUMENTS

| | | | | |
|---|---|---|---|---|
| 5,487,390 | A * | 1/1996 | Cohen | B01J 13/14 600/458 |
| 10,213,424 | B2 | 2/2019 | Cuine et al. | |
| 2007/0269492 | A1* | 11/2007 | Steen | A61P 25/34 424/440 |

FOREIGN PATENT DOCUMENTS

| | | | |
|---|---|---|---|
| WO | WO-2014137385 A1 * | 9/2014 | A61K 31/485 |

OTHER PUBLICATIONS

Steger et al. (Journul of Clinical Pharmacy and Therapeutics, 21:73-78, 1996).*
Prince (Terminal Sterilization of Sterile Filtered Products from | Prince Sterilization Services, Jan. 2021).*
Palladon injection formulation from Mundipharma Pharmaceuticals (Public assessment report of the medicine evaluation board in the Netherlands, Nov. 2012).*
Baniasadi et al. (Braz. J Infect. 2013, 17 (1): 69-73).*
Palash Chandra Das (Concept of Terminal Sterilization, 2019).*
Duncan (Pharmaceutical Development and Technology, 3(4), 527-534, 1998).*
Fresenius Kabi, Package Insert for Diluadid® Injection (updated Oct. 7, 2019), 79 pages.
West-Ward Pharmaceuticals, Package Insert for Hydromorphone Hydrochloride Injection, USP (updated Dec. 10, 2018), 11 pages.
Vermeire & Remon, Int. J. Pharmaceutics, 187:17-51 (1999).

* cited by examiner

*Primary Examiner* — Bong-Sook Baek
(74) *Attorney, Agent, or Firm* — Neal, Gerber & Eisenberg LLP

(57) ABSTRACT

The present disclosure relates to a multi-dose vial presentation for hydromorphone. In particular, the present disclosure relates to terminally sterilized liquid formulations comprising hydromorphone hydrochloride packaged in a multi-dose glass vial. The present disclosure also relates to methods of treating patients by administration of such formulations and glass vials containing such formulations.

8 Claims, 1 Drawing Sheet

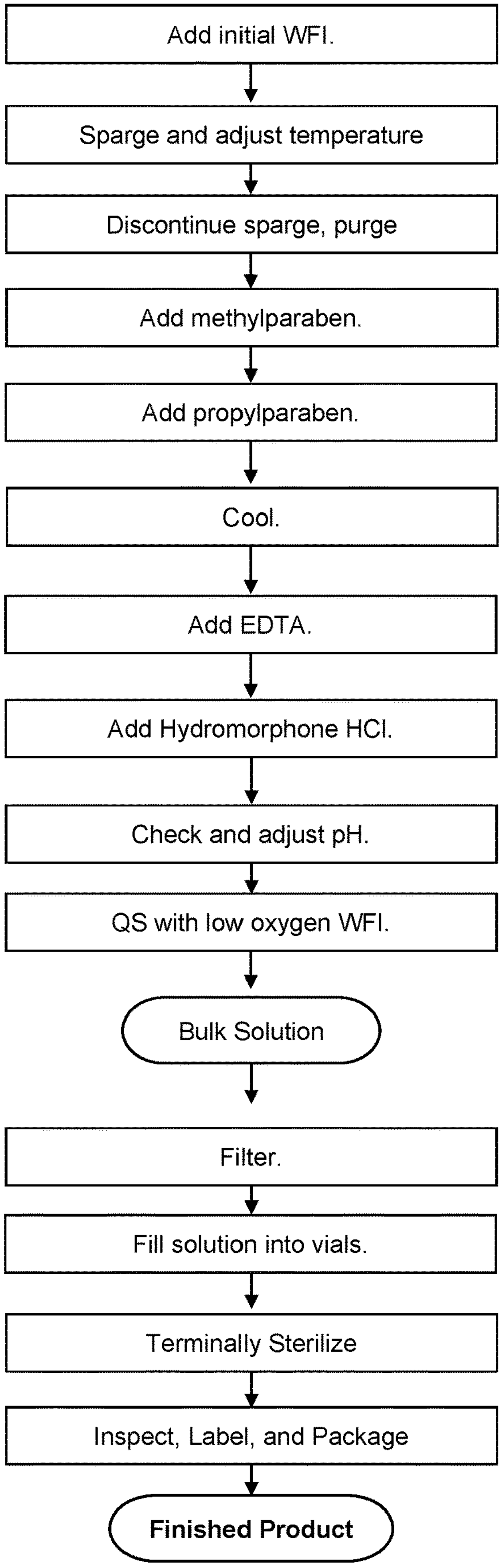
Add initial WFI.
Sparge and adjust temperature
Discontinue sparge, purge
Add methylparaben.
Add propylparaben.
Cool.
Add EDTA.
Add Hydromorphone HCl.
Check and adjust pH.
QS with low oxygen WFI.
Bulk Solution
Filter.
Fill solution into vials.
Terminally Sterilize
Inspect, Label, and Package
Finished Product

HYDROMORPHONE FORMULATIONS FOR MULTI-DOSE PRODUCTS

TECHNICAL FIELD

The present invention relates to multi-dose parenteral liquid formulations comprising hydromorphone or a pharmaceutically acceptable salt thereof, methods for preparing such formulations, methods for using such formulations, and multi-dose vials filled with such formulations.

BACKGROUND

Hydromorphone is a semisynthetic phenanthrene alkaloid of opium; it is classified pharmacologically as a narcotic analgesic. Hydromorphone is indicated for the management of pain severe enough to require an opioid analgesic and for which alternate treatments are inadequate. Hydromorphone is typically used in the hydrochloride salt form.

Current hydromorphone hydrochloride products include an aseptically filled liquid product packaged in glass vials. The vial product is formulated at 2 mg/mL and marketed in 1 mL and 20 mL fills. The 20 mL fill product (40 mg/20 mL) is a multi-dose vial and has a pH range of 4.5 to 4.7. Additional hydromorphone hydrochloride products include 1 mL single-dose prefilled syringes containing 0.2 mg/mL, 1 mg/mL, or 2 mg/mL hydromorphone hydrochloride.

Single-dose products, such as single-dose vials or single-dose syringes, are for use for only a single patient as part of a single case, procedure, or injection. There have been multiple outbreaks resulting from healthcare personnel using single-dose or single-use vials for multiple patients. If a single-dose product has been opened or accessed (e.g., needle-punctured) the product should be discarded according to the time the manufacturer specifies for the opened vial or at the end of the case/procedure for which it is being used, whichever comes first. It should not be stored for future use. As such, single-dose products contribute to waste in the healthcare system because unused drugs are being discarded.

A multi-dose product typically contains liquid medication intended for parenteral administration (injection or infusion) and contains more than one dose of medication. Multi-dose products can be dedicated to a single patient or used for more than one patient.

Care must be taken to ensure that multi-dose products are sterile and remain sterile throughout the lifespan of the product. Thus, multi-dose products typically contain an antimicrobial preservative to help prevent the growth of bacteria.

Additionally, certain pharmaceutical solutions can be sterilized by heat treatment. However, it is known that for formulations containing heat-sensitive active ingredients like hydromorphone, heat treatment is counterproductive because it leads to an unacceptable increase in degradation products brought on by the excessive use of heat in the sterilization process. Indeed, WO2014/137385 ("Foster") demonstrated that heat-labile hydromorphone undergoes transformations to undesirable degradation products, particularly 2,2'-bishydromorphone (commonly known as pseudo-hydromorphone, PHM) during the terminal sterilization process. Foster filled amber 20 cc glass vials with 10 mg/mL hydromorphone hydrochloride solutions (designated A-E) and terminally sterilized the filled vials. Foster demonstrated that the level of known impurities (and in particular PHM), unknown impurities at 0.80 relative retention time (RRT), and total impurities for its terminally sterilized solutions A-E were higher at each day tested as compared to a non-terminally sterilized control, demonstrating that terminal sterilization of its hydromorphone hydrochloride solutions adversely impacted stability of the solutions. Foster instead proposes aseptic processing as an alternative to terminal sterilization.

Thus, there remains a need for multi-dose injectable formulations of hydromorphone that offer long-term storage stability and can be terminally sterilized after filling.

SUMMARY OF THE INVENTION

This disclosure is directed to multi-dose parenteral liquid formulations comprising hydromorphone or a pharmaceutically acceptable salt thereof such as hydromorphone hydrochloride. These multi-dose formulations have been terminally sterilized in an impermeable container, such as a sealed glass vial, and are stable upon long-term storage. As disclosed herein, terminally sterilized hydromorphone hydrochloride liquid formulations in impermeable containers are stable upon long-term storage at room temperature such as from about 20° C. to about 25° C.

In one aspect, this disclosure provides a terminally sterilized hydromorphone hydrochloride packaged in a multi-dose glass vial. In certain embodiments, the concentration of hydromorphone hydrochloride is 2.0 mg/mL, such as 40 mg in 20 mL packaged in a 20 mL clear glass vial.

This disclosure provides a multi-dose parenteral liquid formulation comprising: (a) hydromorphone hydrochloride; (b) a preservative; and (c) a stabilizing agent. The liquid formulation has a pH of 3.5 to 5.5. The liquid formulation has been terminally sterilized in a glass vial and is stable for at least 24 weeks when stored at 40° C.±2° C. and 75% relative humidity (RH)±5% RH or at 25° C.±2° C. and 60% relative humidity (RH)±5% RH. In certain embodiments, the liquid formulation has a pH of 3.5 to 4.5, a pH of 3.6 to 4.4, a pH of 3.7 to 4.3, a pH of 3.8 to 4.2, or a pH of 3.9 to 4.1.

In certain embodiments, the preservative comprises a paraben. In certain embodiments, the preservative comprises methylparaben and propylparaben and, optionally, in a ratio of methylparaben to propylparaben that is from about 3 to 1 to about 10 to 1. In certain embodiments, the liquid formulation has not more than 0.4% w/w, not more than 0.3% w/w, not more than 0.2% w/w, or not more than 0.1% w/w of a paraben degradant such as 4-hydroxybenzoic acid. In some such embodiments, the liquid formulation has not more than 0.4% w/w, not more than 0.3% w/w, not more than 0.2% w/w, or not more than 0.1% w/w of 4-hydroxybenzoic acid after storage for up to 24 weeks at 25° C.±2° C. and 60% relative humidity (RH)±5% RH.

In certain embodiments, the stabilizing agent comprises a chelating agent and/or an antioxidant. In certain embodiments, the stabilizing agent comprises ethylenediaminetetraacetic acid (EDTA). In some such embodiments, the liquid formulation comprises about 0.5 mg/mL ethylenediaminetetraacetic acid (EDTA).

In certain embodiments, the liquid formulation comprises from about 2 mg/mL of hydromorphone hydrochloride. In certain embodiments, the liquid formulation retains at least 95% w/w of the hydromorphone hydrocholoride and has not more than 0.2% w/w of total related substances after storage at 25° C.±2° C. and 60% RH±5% RH for up to 24 weeks.

In certain embodiments, the liquid formulation has not more than 0.3% w/w of 7-hydroperoxylhydromorphone and 7-hydroxylhydromorphone after storage for up to 24 weeks at 40° C.±2° C. and 75% relative humidity (RH)±5% RH. In some such embodiments, the liquid formulation has a pH less than 4.5, such as a pH of 3.6 to 4.4, a pH of 3.7 to 4.3, a pH of 3.8 to 4.2, or a pH of 3.9 to 4.1.

In certain embodiments, the liquid formulation has not more than 0.2% w/w of 7-hydroperoxylhydromorphone and 7-hydroxylhydromorphone after storage for up to 24 weeks at 25° C.±2° C. and 60% relative humidity (RH)±5% RH. In some such embodiments, the liquid formulation has a pH less than 4.5, such as a pH of 3.6 to 4.4, a pH of 3.7 to 4.3, a pH of 3.8 to 4.2, or a pH of 3.9 to 4.1.

This disclosure provides a multi-dose parenteral liquid formulation comprising: (a) 2.0 mg/mL of hydromorphone hydrochloride; (b) 0.5 mg/mL of edetate disodium; (c) 1.8 mg/mL of methylparaben; and (d) 0.2 mg/mL of propylparaben. The liquid formulation has a pH of 3.7 to 4.3. The liquid formulation has been terminally sterilized in a glass vial and is stable for at least 24 weeks when stored at 40° C.±2° C. and 75% relative humidity (RH)±5% RH or at 25° C.±2° C. and 60% relative humidity (RH)±5% RH. In certain embodiments, the liquid formulation has a pH of 3.9 to 4.1.

In certain embodiments, the liquid formulation has not more than 0.4% w/w, not more than 0.3% w/w, not more than 0.2% w/w, or not more than 0.1% w/w of a paraben degradant such as 4-hydroxybenzoic acid. In some such embodiments, the liquid formulation has not more than 0.4% w/w, not more than 0.3% w/w, not more than 0.2% w/w, or not more than 0.1% w/w of 4-hydroxybenzoic acid after storage for up to 24 weeks at 25° C.±2° C. and 60% relative humidity (RH)±5% RH.

In certain embodiments, the liquid formulation retains at least 95% w/w of the hydromorphone hydrocholoride and has not more than 0.2% w/w of total related substances after storage at 25° C.±2° C. and 60% RH±5% RH for up to 24 weeks.

In certain embodiments, the liquid formulation has not more than 0.2% w/w of 7-hydroperoxylhydromorphone and 7-hydroxylhydromorphone after storage for up to 24 weeks at 40° C.±2° C. and 75% relative humidity (RH)±5% RH. In some such embodiments, the liquid formulation has a pH of 3.8 to 4.2 or a pH of 3.9 to 4.1.

In certain embodiments, the liquid formulation has not more than 0.2% w/w of 7-hydroperoxylhydromorphone and 7-hydroxylhydromorphone after storage for up to 24 weeks at 25° C.±2° C. and 60% relative humidity (RH)±5% RH. In some such embodiments, the liquid formulation has a pH of 3.8 to 4.2 or a pH of 3.9 to 4.1.

This disclosure also provides a glass vial filled with the liquid formulation described herein. In certain embodiments, the glass vial has a headspace comprising not more than 8% oxygen.

This disclosure also provides methods for making the multi-dose parenteral liquid formulations described herein. The methods comprise preparing a bulk solution comprising hydromorphone hydrochloride, filling the bulk solution into an impermeable container, and terminally sterilizing the bulk solution in the impermeable container.

The disclosure also provides methods for the management of pain using the multi-dose parenteral liquid formulations described herein. The methods comprise parenterally administering to a subject in need of management of pain the multi-dose parenteral liquid formulations described herein.

The disclosure also provides impermeable containers filled with the multi-dose parenteral liquid formulations described herein. The impermeable containers and their contents have been terminally sterilized. An exemplary impermeable container is a clear glass vial sealed with a halobutyl stopper.

These and other objects of the invention are described in the following paragraphs. These objects should not be deemed to narrow the scope of the invention.

BRIEF DESCRIPTION OF THE DRAWINGS

FIG. 1 is a process flow diagram for the manufacture of a terminally sterilized hydromorphone hydrochloride liquid formulation in a glass vial.

DETAILED DESCRIPTION OF THE INVENTION

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. DEFINITIONS

As used in the specification and the appended claims, unless specified to the contrary, the following terms have the meaning indicated:

The term "about" refers generally to a range of numerical values (e.g., ±5 to 10% of the recited value) that one of ordinary skill in the art would consider equivalent to the recited value. Ranges can be expressed herein as from "about" one particular value, and/or to "about" another particular value. When such a range is expressed, the range is inclusive of the recited values.

The term "antioxidant" refers to a substance that acts to inhibit or delay oxidation.

The term "chelating agent" refers to a substance that can form at least two coordinate covalent bonds with a metal ion to form a complex including those compounds that prevent or delay oxidation.

The term "initial" when used in connection with a given parameter such as osmolality, pH, hydromorphone hydrochloride content, or impurities refers to that parameter at the time the hydromorphone hydrochloride composition is filled into the impermeable container, prior to subjecting the impermeable container and hydromorphone hydrochloride composition to terminal sterilization.

The term "pharmaceutically acceptable" is used adjectivally to mean that the modified noun is appropriate for use as a pharmaceutical product for human use or as a part of a pharmaceutical product for human use.

The term "stabilizing agent" refers to a substance that acts to inhibit or delay degradation and/or oxidation, for example, by controlling those substances (e.g., metals) that may cause oxidation. Exemplary stabilizing agents include chelating agents, such as ethylenediamine tetraacetic acid (EDTA) as well as other compounds having carboxylic acid groups including hydroxycarboxylic acids such as glycolic acid, gluconic acid, and citric acid.

The term "subject" includes humans and other primates as well as other mammals. The term subject includes, for example, a patient, such as a cancer patient or a post-operative patient, suffering from or believed to be suffering from moderate to severe pain. In certain embodiments, the subject is a human.

The terms "treat", "treating" and "treatment" refer to a method of alleviating or abrogating a condition, disorder, or disease and/or the attendant symptoms thereof.

B. DRUG SUBSTANCE

Liquid formulations disclosed herein comprise at least one active pharmaceutical ingredient: hydromorphone or a pharmaceutically acceptable salt thereof. In one particular embodiment, the pharmaceutically acceptable salt of hydromorphone is hydromorphone hydrochloride.

Hydromorphone hydrochloride is chemically identified as 4,5α-epoxy-3-hydroxy-17-methylmorphinan-6-one hydrochloride. The molecular weight of hydromorphone hydrochloride is 321.80 and its molecular formula is $C_{17}H_{19}NO_3 \cdot HCl$. Hydromorphone hydrochloride has the following chemical structure:

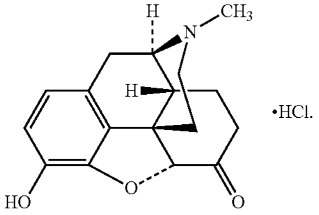

$(C_{17}H_{19}NO_3) \cdot HCl$;
MW: 321.80 g/mol

Methods for synthesizing hydromorphone and a pharmaceutically acceptable salts thereof are known in the art and described, for example, in U.S. Pat. No. 6,589,960, the contents of which are herein incorporated by reference.

Other suitable hydromorphone salts include any water soluble salt of hydromorphone such as hydromorphone sulfate.

In certain embodiments, hydromorphone hydrochloride is present in the liquid formulation in an amount from about 0.5 mg/mL to about 10.0 mg/mL, alternatively from about 1.0 mg/mL to about 5.0 mg/mL, or alternatively from about 1.5 mg/mL to about 2.5 mg/mL. In some such embodiments, the liquid formulation comprises 2.0 mg/mL of hydromorphone hydrochloride.

C. LIQUID FORMULATIONS

This disclosure provides a liquid formulation that is suitable for terminal sterilization in an impermeable container and is stable upon long-term storage following such terminal sterilization. The liquid formulation may contain one or more excipients such as a stabilizing agent, a preservative, and/or a pH adjusting agent.

In certain embodiments, the liquid formulation has a pH in the range of about 3.5 to about 4.5, alternatively from about 3.5 to about 4.4, alternatively from about 3.5 to about 4.3, alternatively from about 3.5 to about 4.2, alternatively from about 3.5 to 4.1. In some such embodiments, the liquid formulation has a pH in the range of about 3.6 to about 4.5, alternatively from about 3.6 to about 4.4, alternatively from about 3.6 to about 4.3, alternatively from about 3.6 to about 4.2, alternatively from about 3.6 to 4.1. In some such embodiments, the liquid formulation has a pH in the range of about 3.7 to about 4.5, alternatively from about 3.7 to about 4.4, alternatively from about 3.7 to about 4.3, alternatively from about 3.7 to about 4.2, alternatively from about 3.7 to 4.1. In some such embodiments, the liquid formulation has a pH in the range of about 3.8 to about 4.5, alternatively from about 3.8 to about 4.4, alternatively from about 3.8 to about 4.3, alternatively from about 3.8 to about 4.2, alternatively from about 3.8 to 4.1. In some such embodiments, the liquid formulation has a pH in the range of about 3.9 to about 4.5, alternatively from about 3.9 to about 4.4, alternatively from about 3.9 to about 4.3, alternatively from about 3.9 to about 4.2, alternatively from about 3.9 to 4.1. In an exemplary embodiment, the liquid formulation has a pH in the range of about 3.7 to about 4.3. In an exemplary embodiment, the liquid formulation has a pH in the range of about 3.8 to about 4.2. In another exemplary embodiment, the liquid formulation has a pH in the range of about 3.9 to about 4.1, preferably about 4.0.

In certain embodiments, the disclosed liquid formulation comprises a pH adjusting agent.

In certain embodiments, the pH of the liquid formulation is adjusted by addition of a pH adjusting agent. The pH adjusting agent that may be, without limitation, an acid such as sulfuric acid, phosphoric acid, or hydrochloric acid, a base such as sodium acetate, sodium bicarbonate, or sodium hydroxide, or a combination thereof.

In certain embodiments, the pH adjusting agent is hydrochloric acid, sodium hydroxide, or a combination thereof.

The concentration of the pH adjusting agent can be any concentration suitable for adjusting the pH, such as, for example, 0.1N acid or base. In certain embodiments, 0.1N hydrochloric acid and/or 0.1N sodium hydroxide are added to obtain the desired pH.

In certain embodiments, the disclosed liquid formulation comprises a stabilizing agent. In certain embodiments, the stabilizing agent is a chelating agent. In certain embodiments, the stabilizing agent is an antioxidant. In certain embodiments, the stabilizing agent is a single ingredient that acts as a chelating agent and/or an antioxidant. In certain embodiments, the stabilizing agent is a combination of two or more ingredients that act as a chelating agent and/or an antioxidant.

Exemplary stabilizing agents that may act as a chelating agent include, but are not limited to, aminopolycarboxylic acids or aminopolycarboxylates such as nitrilotriacetic acid (NTA), ethylenediaminetetraacetic acid (EDTA), diethylenetriaminepentaacetic acid (DTPA), and salts thereof; pentetate salts such as pentasodium pentetate and the acid form thereof; and etidronate salts such as tetrasodium etidronate and the acid form thereof.

Exemplary stabilizing agents that may act as an antioxidant include, but are not limited to, a metabisulfite such as sodium metabisulfite or potassium metabisulfite, butylated hydroxytoluene (BHT), and ascorbic acid.

Exemplary stabilizing agents include, but are not limited to, aminopolycarboxylic acids or aminopolycarboxylates such as ethylenediaminetetraacetic acid (EDTA), diethylenetriaminepentaacetic acid (DTPA), and ethylene glycol-bis (β-aminoethyl ether)-N,N,N',N'-tetraacetic acid (EGTA). In some such embodiments, the stabilizing agent comprises EDTA. The term "ethylenediaminetetraacetic acid" or "EDTA" encompasses salt and/or hydrate forms including, but not limited to, dipotassium edetate, disodium edetate, edetate calcium disodium, sodium edetate, trisodium edetate, potassium edetate, and disodium edetate dihydrate (or disodium EDTA dihydrate or EDTA disodium salt). In some such embodiments, the stabilizing agent comprises disodium edetate dihydrate.

In certain embodiments, the stabilizing agent is present in the liquid formulation in an amount from about 0.001% to about 1.0% (w/v). For example, the stabilizing agent may be present in amount from about 0.005% to about 0.5% (w/v) or from about 0.01% to about 0.1% (w/v). In some such embodiments, the amount of stabilizing agent is about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), or about 0.1% (w/v).

In certain embodiments, the stabilizing agent comprises, or consists of, EDTA, such as disodium edetate dihydrate. In some such embodiments, the liquid formulation comprises from about 0.1 to about 1.0 mg/mL EDTA, alternatively from about 0.25 to about 0.75 mg/mL EDTA, or alternatively from about 0.45 to about 0.55 mg/mL EDTA. In some such embodiments, the liquid formulation comprises about 0.5 mg/mL EDTA. In an exemplary embodiment, the liquid formulation comprises about 0.5 mg/mL disodium edetate dihydrate.

In certain embodiments, the disclosed liquid formulation comprises a preservative. Exemplary preservatives include, but are not limited to, benzyl alcohol, methylparaben, ethylparaben, propylparaben, butylparaben, benzalkonium chloride, or a combination thereof. In certain embodiments, the preservative comprises methylparaben and/or propylparaben. In some such embodiments, the preservative comprises a combination of methylparaben and propylparaben.

In certain embodiments, the preservative is present in the liquid formulation in an amount from about 0.001% to about 1.0% (w/v). For example, the preservative may be present in amount from about 0.005% to about 0.5% (w/v) or from about 0.01% to about 0.4% (w/v) or from about 0.02% to about 0.2% (w/v). In some such embodiments, the amount of preservative is about 0.02% (w/v), about 0.04% (w/v), about 0.06% (w/v), about 0.08% (w/v), about 0.1% (w/v), about 0.12% (w/v), about 0.14% (w/v), about 0.16% (w/v), about 0.18% (w/v), about 0.2% (w/v), about 0.22% (w/v), or about 0.24% (w/v).

In certain embodiments, the preservative comprises methylparaben and propylparaben. In some such embodiments, the liquid formulation comprises from about 1.0 to about 3.0 mg/mL methylparaben and propylparaben, alternatively from about 1.5 to about 2.5 mg/mL methylparaben and propylparaben, or alternatively from about 1.75 to about 2.25 mg/mL methylparaben and propylparaben. In some such embodiments, the liquid formulation comprises about 2.0 mg/mL methylparaben and propylparaben. In an exemplary embodiment, the liquid formulation comprises about 1.8 mg/mL methylparaben and about 0.2 mg/mL propylparaben.

In certain embodiments, the preservative comprises methylparaben and propylparaben, wherein the ratio of methylparaben to propylparaben is from about 3 to 1 to about 10 to 1. In some such embodiments, the ratio of methylparaben to propylparaben is about 3 to 1, alternatively about 4 to 1, alternatively about 5 to 1, alternatively about 6 to 1, alternatively about 7 to 1, alternatively about 8 to 1, alternatively about 9 to 1, or alternatively about 10 to 1. In an exemplary embodiment, the ratio of methylparaben to propylparaben is about 9 to 1.

In certain embodiments, the liquid formulation contains a stabilizing agent and/or a preservative. In some such embodiments, the liquid formulation contains a stabilizing agent and a preservative.

In certain embodiments, the liquid formulation further comprises a buffer system. The buffer system may be, without limitation, a phosphate buffer, a citrate buffer, an acetate buffer, a histidine buffer, or a combination thereof. However, in certain embodiments, the liquid formulation is substantially free of a buffer system. In some such embodiments, the liquid formulation is substantially free of a citrate buffer.

Thus, in one embodiment, the liquid formulation does not contain any buffer system or buffer system components (e.g., sodium citrate and citric acid). It should be noted, however, that although the preferred liquid formulation does not contain any buffer system or buffer system components, a small amount of such components may be present in the formulation, for example, as trace contaminants introduced by other ingredients.

This disclosure provides a multi-dose parenteral liquid formulation comprising hydromorphone hydrochloride, a stabilizing agent, a preservative, optionally one or more pH adjusting agents, and water for injection. An exemplary embodiment is provided in Table 1 below.

TABLE 1

| Ingredient | Function | Amount per mL |
|---|---|---|
| Hydromorphone Hydrochloride, USP | Active Ingredient | 2.0 mg |
| Edetate Disodium, USP | Stabilizing Agent | 0.5 mg |
| Methylparaben, NF | Preservative | 1.8 mg |
| Propylparaben, NF | Preservative | 0.2 mg |
| Sodium Hydroxide | pH adjustment | pH adjustment |
| Hydrochloric Acid | pH adjustment | pH adjustment |
| Water for Injection, USP | Aqueous Vehicle | q.s. to 1 ml |

D. IMPERMEABLE CONTAINERS

The hydromorphone hydrochloride formulations disclosed herein are ideally multi-dose formulations for parenteral administration. The multi-dose formulations comprise an aqueous liquid and are stored in a pharmaceutically acceptable container, for example, an impermeable container (e.g., a glass vial with a suitable stopper).

Exemplary container components include, but are not limited to, clear or amber glass vials and an elastomer stopper. Preferably, the materials for the container and container components are suitable to withstand aseptic filling and not deform during terminal sterilization. In certain embodiments, the impermeable container comprises a vial made from borosilicate glass, which is characterized by excellent hydrolytic stability and high thermal shock resistance, such as a Type 1 vial available from Bormioli Pharma. In certain embodiments, the impermeable container comprises a stopper made from an elastomer such as halobutyl (e.g., chlorobutyl or bromobutyl) elastomer. Suitable stoppers include ready-to-sterilize (RTS) stoppers. An exemplary stopper is made from 4432/50 a premium quality chlorobutyl elastomer, such as those available from West Pharmaceutical Services.

In certain embodiments, the hydromorphone hydrochloride liquid formulation is filled into the container under an inert gas, preferably nitrogen, overlay to provide a headspace comprising the inert gas. For example, the hydromorphone hydrochloride liquid formulation may be provided in a container having a nitrogen headspace. In some such embodiments, the hydromorphone hydrochloride liquid formulation is provided in a container having a headspace comprising at least 88% nitrogen, at least 90% nitrogen, or at least 92% nitrogen. In some such embodiments, the hydromorphone hydrochloride liquid formulation is provided in a container having a headspace comprising at least 92% nitrogen. In some such embodiments, the oxygen content of the headspace is reduced relative to ambient air. In some such embodiments, the hydromorphone hydrochloride liquid formulation is provided in a container having a headspace comprising not more than 12%, not more than 10%, or not more than 8% oxygen. In some such embodiments, the hydromorphone hydrochloride liquid formulation is provided in a container having a headspace comprising not more than 8% oxygen. In some such embodiments, the hydromorphone hydrochloride liquid formulation is provided in a container having a headspace comprising 92% nitrogen and 8% oxygen.

In certain embodiments, the hydromorphone hydrochloride liquid formulation is prepared as a 20 mL fill packaged in a 20 mL impermeable container, such as a clear glass vial with a halobutyl elastomer stopper.

Exemplary components of an impermeable container for hydromorphone hydrochloride are provided in Table 2 below.

TABLE 2

| Component | Description |
|---|---|
| Vial | 20 mL, Type 1, Flint, 20 mm, Clear Untreated Vial |
| Stopper | 20 mm, S127, 4432/50 gray Westar ®RTS Stopper |

E. TERMINAL STERILIZATION

General procedures for filling the liquid formulation into the impermeable containers and their subsequent processing, for example, terminal sterilization, are known in the art.

Processing techniques of the formulations filled in an impermeable container preferably use a sterilization process to destroy or eliminate any microorganisms that may be present in the hydromorphone hydrochloride formulations following preparation. For example, terminal sterilization can be used to destroy or eliminate any microorganisms that may be present in the impermeable container containing the hydromorphone hydrochloride liquid formulation. An autoclave is commonly used to accomplish terminal heat-sterilization of drug products in their final packaging.

In certain embodiments, the liquid formulation has an initial pH in the range of about 3.5 to about 4.5, alternatively from about 3.5 to about 4.4, alternatively from about 3.5 to about 4.3, alternatively from about 3.5 to about 4.2, alternatively from about 3.5 to 4.1. In some such embodiments, the liquid formulation has an initial pH in the range of about 3.6 to about 4.5, alternatively from about 3.6 to about 4.4, alternatively from about 3.6 to about 4.3, alternatively from about 3.6 to about 4.2, alternatively from about 3.6 to 4.1. In some such embodiments, the liquid formulation has an initial pH in the range of about 3.7 to about 4.5, alternatively from about 3.7 to about 4.4, alternatively from about 3.7 to about 4.3, alternatively from about 3.7 to about 4.2, alternatively from about 3.7 to 4.1. In some such embodiments, the liquid formulation has an initial pH in the range of about 3.8 to about 4.5, alternatively from about 3.8 to about 4.4, alternatively from about 3.8 to about 4.3, alternatively from about 3.8 to about 4.2, alternatively from about 3.8 to 4.1. In some such embodiments, the liquid formulation has an initial pH in the range of about 3.9 to about 4.5, alternatively from about 3.9 to about 4.4, alternatively from about 3.9 to about 4.3, alternatively from about 3.9 to about 4.2, alternatively from about 3.9 to 4.1. In an exemplary embodiment, the liquid formulation has an initial pH in the range of about 3.7 to about 4.3. In an exemplary embodiment, the liquid formulation has an initial pH in the range of about 3.8 to about 4.2. In another exemplary embodiment, the liquid formulation has an initial pH in the range of about 3.9 to about 4.1, preferably about 4.0.

In certain embodiments, the impermeable container filled with the liquid formulation containing hydromorphone hydrochloride is terminally sterilized using an autoclave, such as water cascade autoclave. The liquid formulations in the impermeable containers can be autoclaved at a temperature ranging from 115° C. to 130° C., preferably at a temperature ranging from 119° C. to 122° C., for a period of time ranging from about 5 to about 30 minutes, alternatively from about 10 to about 20 minutes, alternatively for about 15 minutes.

In certain embodiments, a terminal sterilization cycle is based on a $D_{121}$-value or decimal reduction time. In some such embodiments, the terminal sterilization cycle is based on a $D_{121}$-value that is less than 2.0, alternatively less than 1.5, such as about 1.1.

In certain embodiments, terminal sterilization can be characterized by specifying a $F_0$ value. The $F_0$ value is the equivalent time in minutes for the specified temperature that gives the same thermal lethality as at 121° C. For example, if a cycle has an $F_0$ value of 15, the sterilization effectiveness of that cycle is equal to 15 minutes at 121° C. regardless of the process temperature and time used in the cycle. In some such embodiments, the $F_0$ is less than 30, such as from about 10 to about 20, alternatively from about 12 to about 18. In some such embodiments, the $F_0$ is about 15. In some such embodiments, the $F_0$ is not more than about 30, alternatively not more than about 25, alternatively not more than about 20.

As described herein, it was observed that the hydromorphone hydrochloride liquid formulations contained in an impermeable container can withstand terminal sterilization cycles up to $F_0$ of 35 minutes. Thus, in some such embodiments, the $F_0$ does not exceed 35. Alternatively, in some such embodiments, the $F_0$ does not exceed 30, 25, or 20.

In certain embodiments, the liquid formulation containing hydromorphone hydrochloride is substantially free of viable microbial contamination after terminal sterilization. Methods for assessing microbial contamination are known in the art and include testing for sterility in accordance with USP <71> using Trypticase Soy Broth (Soybean-Casein Digest Medium), which is suitable for the culture of both fungi and aerobic bacteria and/or Fluid Thioglycolate Medium, which is a medium primarily intended for the culture of anaerobic bacteria.

F. COMPOUNDING PROCEDURE

In one aspect, this disclosure provides a method for manufacturing a terminally sterilized, 2.0 mg/mL presentation of hydromorphone hydrochloride packaged in a multi-dose container.

In certain embodiments, compounding takes place in a controlled environment in a stainless steel vessel equipped with a mixer.

FIG. 1 depicts an exemplary process flow diagram for the manufacture of a terminally sterilized hydromorphone hydrochloride formulation packaged in a multi-dose container.

At step 1, add water for injection (WFI)—80% of final weight—to an empty compounding vessel. Begin mixing at a low rpm.

At step 2, begin a nitrogen sparge; continue sparge for not less than 30 minutes or until dissolved oxygen is not more than 1 ppm; temperature is 48° C. to 52° C.

At step 3, discontinue sparge and start purge. Continuously purge throughout compounding.

At step 4, discontinue purge, add calculated amount of methylparaben to the compounding vessel (e.g., to achieve a final concentration of 1.8 g/L), reinstate the purge, and mix for not less than 20 minutes or until dissolved.

At step 5, discontinue purge, add calculated amount of propylparaben to the compounding vessel (e.g., to achieve a final concentration of 0.2 g/L), reinstate the purge, and mix for not less than 20 minutes or until dissolved.

At step 6, cool the solution to a temperature of 20° C. to 25° C.

At step 7, discontinue purge, add calculated amount of EDTA (e.g., disodium edetate dihydrate) to the compounding vessel (e.g., to achieve a final concentration of 0.5 g/L), reinstate the purge, and mix for not less than 5 minutes or until dissolved.

At step 8, discontinue purge, add calculated amount of hydromorphone hydrochloride, USP to the compounding vessel (e.g., to achieve a final concentration of 2.0 g/L), reinstate the purge, and mix for not less than 5 minutes or until dissolved.

At step 9, measure pH and adjust to 3.9 to 4.1 (Target 4.0) using 0.1N Sodium Hydroxide or 0.1N Hydrochloric Acid solution. Mix for at least 5 minutes between each addition.

At step 10, add WFI to QS until final solution weight is reached and mix for at least 20 minutes.

At step 11, discontinue purge and blanket the bulk solution with nitrogen.

At step 12, the bulk solution is filtered (e.g., 0.2 μm, 10" filter).

At step 13, filtered bulk solution is filled into 20 mL glass vials under an oxygen headspace of not more than 8%.

At step 14, filled vials are terminally sterilized at a temperature of 121° C. and a set $F_0$ of 15.0 minutes.

At step 15, terminally sterilized vials are inspected, labeled, and packaged.

G. STABILITY

Hydromorphone hydrochloride is heat sensitive and reactive with air and other oxidizing agents. Degradation products of hydromorphone hydrochloride include 2,2'-bishydromorphone, hydromorphone N-oxide, 7-hydroperoxyl hydromorphone, and 7-hydroxyl hydromorphone. Hydromorphone hydrochloride degradants may be a source of degradants in the drug product.

Preservatives may also be a source of degradants in the drug product. Degradation products of preservatives, such as parabens, include 4-hydroxybenzoic acid.

In at least one aspect, the terminally sterilized liquid formulations disclosed herein and comprising a stabilizing agent are stable during, for example, storage, distribution, and the duration of the product's shelf-life (e.g., up to two years at room temperature/ambient conditions). A stable terminally sterilized liquid formulation may, for example, exhibit less degradation of the active ingredient and/or low amounts of degradation products compared to an otherwise identical formulation without the stabilizing agent. Assay and degradation product determination of liquid formulations may be performed using High Performance Liquid Chromatography ("HPLC") with UV detection.

In certain embodiments, the terminally sterilized hydromorphone hydrochloride liquid formulation packaged in an impermeable container such as a glass vial with a suitable elastomer stopper meets release specifications and/or shelf-life specifications for hydromorphone hydrochloride, particular related substances, total related substances, and/or individual unknown impurities. In some such embodiments, the terminally sterilized hydromorphone hydrochloride liquid formulation is packaged in a container having a headspace comprising not more than 8% oxygen. In some such embodiments, the amount of hydromorphone hydrochloride, related substances, and/or individual unknown impurities is determined by HPLC.

Exemplary release specifications for hydromorphone hydrochloride are at least 93%, at least 94%, at least 95%, at least 96%, at least 97%, at least 98%, or at least 99% of the specified amount of hydromorphone hydrochloride (e.g., 2.0 mg/mL). In certain embodiments, the release specification for hydromorphone hydrochloride is from about 90% to about 110%, or from about 95% to about 105%, or from about 98% to about 104% of the specified amount of hydromorphone hydrochloride (e.g., 2.0 mg/mL).

Exemplary release specifications for related compounds, such as 2,2'-bishydromorphone, hydromorphone N-oxide, and 7-hydroperoxyl hydromorphone and 7-hydroxyl hydromorphone (the 7-substituted hydromorphone compounds can be considered together) are not more than 0.5%, not more than 0.4%, not more than 0.3%, or not more than 0.2% of the particular related compound(s).

Exemplary release specifications for preservative degradants, such as 4-hydroxybenzoic acid, are not more than 0.5%, not more than 0.4%, not more than 0.3%, or not more than 0.2% of the particular degradant(s).

Exemplary release specifications for total related compounds, which includes at least 2,2'-bishydromorphone and hydromorphone N-oxide as well as individual unknown impurities, are not more than 3.0%, not more than 2.5%, not more than 2.0%, not more than 1.5%, not more than 1.0%, or not more than 0.5%.

Exemplary shelf-life specifications for hydromorphone hydrochloride are at least 90%, at least 91%, at least 92%, at least 93%, at least 94%, at least 95%, at least 96%, at least 97%, or at least 98% of the specified amount of hydromorphone hydrochloride (e.g., 2.0 mg/mL). In certain embodiments, the shelf-life specification for hydromorphone hydrochloride is from about 90% to about 110% or from about 95% to about 105% of the specified amount of hydromorphone hydrochloride (e.g., 2.0 mg/mL).

Exemplary shelf-life specifications for related compounds, such as 2,2'-bishydromorphone, hydromorphone N-oxide, and 7-hydroperoxyl hydromorphone and 7-hydroxyl hydromorphone (the 7-substituted hydromorphone compounds can be considered together) are not more than 1.0%, not more than 0.9%, not more than 0.8%, not more than 0.7%, not more than 0.6%, not more than 0.5%, not more than 0.4%, not more than 0.3%, or not more than 0.2% of the particular related compound(s). In some such embodiments, shelf-life specifications for known related compounds are not more than 1.0%, not more than 0.9%, not more than 0.8%, not more than 0.7%, not more than 0.6%, not more than 0.5%, not more than 0.4%, not more than 0.3%, or not more than 0.2% of the particular known related compound(s). In some such embodiments, shelf-life specifications for unknown related compounds are not more than 1.0%, not more than 0.9%, not more than 0.8%, not more than 0.7%, not more than 0.6%, not more than 0.5%, not more than 0.4%, not more than 0.3%, or not more than 0.2% of the particular unknown related compound(s).

Exemplary shelf-life specifications for total related compounds, which includes at least 2,2'-bishydromorphone and hydromorphone N-oxide as well as individual unknown impurities, are not more than 3.0%, not more than 2.5%, not more than 2.0%, not more than 1.5%, not more than 1.0%, or not more than 0.5%.

Stability of a terminally sterilized hydromorphone hydrochloride liquid formulation packaged in a multi-dose vial may be assessed following storage for at least two weeks, at least four weeks, at least 8 weeks, at least 3 months, at least 6 months, at least 12 months, at least 15 months, at least 18 months, or at least 24 months. In particular, pH, osmolality, hydromorphone concentration, degradation products or other impurities, may be assessed after storage for about 2, 4, and/or 8 weeks and/or about 3, 6, 9, 12, 15, 18, 24, 36, and/or 48 months. Storage conditions may be long term, intermediate, accelerated, or stress conditions. In particular, storage conditions may be, for example, 25° C.±2° C. and 60% relative humidity (RH)±5% RH, 30° C.±2° C. and 65% RH±5% RH, and/or 40° C.±2° C. and 75% RH±5% RH. Stress conditions can include a temperature above the temperature used for accelerated testing (e.g., 50° C. or 60° C.). Specific storage conditions described herein, and particularly relative humidity values, are merely exemplary as stability studies for products stored in impermeable containers can be conducted under any controlled or ambient humidity condition.

In certain embodiments, storage of the terminally sterilized hydromorphone hydrochloride liquid formulation packaged in a multi-dose vial is at 25° C.±2° C. and 60%±5% relative humidity for between about 1 month and about 48 months, between about 2 months and about 36 months, or between about 3 months and about 24 months. In certain embodiments, storage of the terminally sterilized hydromorphone hydrochloride liquid formulation packaged in an impermeable container is at 25° C.±2° C. and 60%±5% relative humidity for up to 3 months, up to 6 months, up to 12 months, up to 15 months, up to 18 months, or up to 24 months. In some such embodiments, storage stability is assessed at about 3, 6, 9, 12, 15, 18, 24, and/or 36 months.

In certain embodiments, storage of the terminally sterilized hydromorphone hydrochloride liquid formulation packaged in a multi-dose vial is at 30° C.±2° C. and 65%±5% relative humidity for between about 1 month and about 24 months or between about 1 month and about 12 months. In certain embodiments, storage of the terminally sterilized hydromorphone hydrochloride liquid formulation packaged in a multi-dose vial is at 30° C.±2° C. and 65%±5% relative humidity for up to 2 months, up to 3 months, up to 6 months, or up to 12 months. In some such embodiments, storage stability is assessed at about 1, 2, 3, 6, and/or 12 months.

In certain embodiments, storage of the terminally sterilized hydromorphone hydrochloride liquid formulation packaged in a multi-dose vial is at 40° C.±2° C. and 75%±5% relative humidity for between about 1 month and about 12 months or between about 1 month and about 6 months. In certain embodiments, storage of the terminally sterilized hydromorphone hydrochloride liquid formulation packaged in a multi-dose vial is at 40° C.±2° C. and 75%±5% relative humidity for up to 2 months, up to 3 months, or up to 6 months. In some such embodiments, storage stability is assessed at about 1, 2, 3, and/or 6 months.

In certain embodiments, storage of the terminally sterilized hydromorphone hydrochloride liquid formulation packaged in a multi-dose vial is at 50° C. for between about 1 week and about 12 weeks or between about 1 week and about 6 weeks. In certain embodiments, storage of the terminally sterilized hydromorphone hydrochloride liquid formulation packaged in a multi-dose vial is at 50° C. for up to 2 weeks, up to 3 weeks, or up to 6 weeks. In some such embodiments, storage stability is assessed at about 2, 4, and/or 8 weeks.

Storage stability assessments may include pH, appearance, hydromorphone concentration, degradation products or other impurities including but not limited to 2,2'-bishydromorphone, hydromorphone N-oxide, 4-hydroxybenzoic acid, and 7-hydroperoxyl hydromorphone and 7-hydroxyl hydromorphone (the 7-substituted hydromorphone compounds can be considered together).

In certain embodiments, the terminally sterilized hydromorphone hydrochloride liquid formulation packaged in a multi-dose vial has a pH in the range of about 3.5 to about 5.5, alternatively, from about 3.5 to 4.5, or alternatively from about 3.8 to about 4.2 after storage for up to 2 weeks, up to 4 weeks, up to 8 weeks, up to 3 months, up to 6 months, up to 9 months, up to 12 months, up to 15 months, up to 18 months, or up to 24 months under long-term storage conditions. In some such embodiments, the terminally sterilized hydromorphone hydrochloride liquid formulation packaged in a multi-dose vial has a pH of about 3.6, about 3.7, about 3.8, about 3.9, or about 4.0 after storage for up to 2 weeks, up to 4 weeks, up to 8 weeks, up to 3 months, up to 6 months, up to 9 months, up to 12 months, up to 15 months, up to 18 months, or up to 24 months under long-term storage conditions.

In certain embodiments, the pH of the terminally sterilized hydromorphone hydrochloride liquid formulation packaged in a multi-dose vial does not materially change over time under long-term storage conditions.

In certain embodiments, the terminally sterilized hydromorphone hydrochloride liquid formulation packaged in a multi-dose vial retains at least 90%, alternatively at least 91%, alternatively at least 92%, alternatively at least 93%, alternatively at least 94%, alternatively at least 95%, alternatively at least 96%, alternatively at least 97%, or alternatively at least 98% of the hydromorphone hydrochloride in the liquid formulation after storage for up to 2 weeks, up to 4 weeks, up to 8 weeks, up to 3 months, up to 6 months, up to 9 months, up to 12 months, up to 15 months, up to 18 months, or up to 24 months under long-term storage conditions as determined by HPLC. In some such embodiments, the terminally sterilized hydromorphone hydrochloride liquid formulation packaged in a multi-dose vial retains from about 90% to about 110%, alternatively from about 95% to about 105%, of the hydromorphone hydrochloride in the liquid formulation after storage for up to 2 weeks, up to 4 weeks, up to 8 weeks, up to 3 months, up to 6 months, up to 9 months, up to 12 months, up to 15 months, up to 18 months, or up to 24 months under long-term storage conditions as determined by HPLC.

In some such embodiments, the amount of hydromorphone hydrochloride retained following storage is with reference to the hydromorphone hydrochloride concentration prior to storage. In some such embodiments, the hydromorphone hydrochloride concentration prior to storage is from about 0.5 mg/mL to about 10.0 mg/mL, alternatively from about 1.0 mg/mL to about 5.0 mg/mL, or alternatively from about 1.5 mg/mL to about 2.5 mg/mL. In some such embodiments, the hydromorphone hydrochloride concentration prior to storage is 2.0 mg/mL. In some such embodiments, the amount of hydromorphone hydrochloride retained following storage is with reference to a product label claim. In some such embodiments, the product label claim for hydromorphone hydrochloride is from about 0.5 mg/mL to about 10.0 mg/mL, alternatively from about 1.0 mg/mL to about 5.0 mg/mL, or alternatively from about 1.5 mg/mL to about 2.5 mg/mL. In some such embodiments, the product label claim for hydromorphone hydrochloride is 2.0 mg/mL.

In certain embodiments, the amount of hydromorphone hydrochloride in the terminally sterilized hydromorphone hydrochloride liquid formulation packaged in a multi-dose vial does not materially change over time under long-term storage conditions.

In certain embodiments, the terminally sterilized hydromorphone hydrochloride liquid formulation packaged in a multi-dose vial contains not more than 1.0%, not more than 0.9%, not more than 0.8%, not more than 0.7%, not more than 0.6%, not more than 0.5%, not more than 0.4%, not more than 0.3%, not more than 0.2%, or not more than 0.1% of any individual specified or unspecified related substance (e.g., degradation products such as 2,2'-bishydromorphone, hydromorphone N-oxide, and 7-hydroperoxyl hydromorphone and 7-hydroxyl hydromorphone (the 7-substituted hydromorphone compounds can be considered together)) after storage for up to 2 weeks, up to 4 weeks, up to 8 weeks, up to 3 months, up to 6 months, up to 9 months, up to 12 months, up to 15 months, up to 18 months, or up to 24 months under long-term storage conditions as determined by HPLC.

In certain embodiments, the terminally sterilized hydromorphone hydrochloride liquid formulation packaged in a multi-dose vial contains not more than 4.0%, not more than 3.0%, not more than 2.0%, not more than 1.0%, or not more than 0.5% total related substances after storage for up to 2 weeks, up to 4 weeks, up to 8 weeks, up to 3 months, up to 6 months, up to 9 months, up to 12 months, up to 15 months, up to 18 months, or up to 24 months under long-term storage conditions as determined by HPLC.

In some such embodiments, the terminally sterilized hydromorphone hydrochloride liquid formulation packaged in a multi-dose vial contains not more than 0.20%, not more than 0.15%, or not more than 0.10% w/w of total related substances after storage for 2, 4, or 8 weeks under long-term storage conditions (e.g., 25° C.±2° C. and 60% RH±5% RH) as determined by HPLC. In some such embodiments, the liquid formulation retains at least 95%, preferably at least 98%, and more preferably at least 99% w/w of the hydromorphone hydrocholoride after storage for 2, 4, or 8 weeks under long-term storage conditions as determined by HPLC.

In certain embodiments, the liquid formulation is stable for at least 2 weeks, at least 4 weeks, at least 8 weeks, at least 3 months, at least 6 months, at least 9 months, at least 12 months, at least 15 months, or at least 18 months when stored at 25° C.±2° C. and 60% relative humidity (RH)±5% RH. In some such embodiments, the liquid formulation is stable for up to 24 months when stored at 25° C.±2° C. and 60% RH±5% RH.

In some such embodiments, the liquid formulation retains at least 90% w/w, preferably at least 95% w/w, and more preferably at least 98% of the hydromorphone hydrochloride and has not more than 10% w/w, preferably not more than 5% w/w, and more preferably not more than 2% w/w of total related substances after storage at 25° C.±2° C. and 60% RH±5% RH for 2, 4, or 8 weeks or 3, 6, 9, 12, 15, 18, or 24 months.

In some such embodiments, the liquid formulation retains at least 90% w/w, preferably at least 95% w/w, and more preferably at least 98% of the hydromorphone hydrochloride and has not more than 0.8% w/w, preferably not more than 0.5% w/w, and more preferably not more than 0.2% w/w of any individual specified or unspecified related substance (e.g., degradation products such as 2,2'-bishydromorphone, hydromorphone N-oxide, and 7-hydroperoxyl hydromorphone and 7-hydroxyl hydromorphone (the 7-substituted hydromorphone compounds can be considered together)) after storage at 25° C.±2° C. and 60% RH±5% RH for 2, 4, or 8 weeks or 3, 6, 9, 12, 15, 18, or 24 months.

In some such embodiments, the pH of the liquid formulation after storage at 25° C.±2° C. and 60% RH 5% RH for 2, 4, or 8 weeks or 3, 6, 9, 12, 15, 18, or 24 months is in the range of about 3.5 to about 5.5, alternatively, from about 3.5 to 4.5, alternatively, from about 3.6 to 4.4, or alternatively from about 3.7 to about 4.3. In an exemplary embodiment, the pH of the liquid formulation after storage at 25° C.±2° C. and 60% RH±5% RH for 2, 4, or 8 weeks or 3, 6, 9, 12, 15, 18, or 24 months is in the range of about 3.8 to about 4.2, preferably about 3.9 to 4.1.

In certain embodiments, the terminally sterilized hydromorphone hydrochloride liquid formulation packaged in a multi-dose vial has a pH in the range of about 3.5 to about 5.5, alternatively, from about 3.5 to 4.5, or alternatively from about 3.8 to about 4.2 after storage for up to 2 weeks, up to 4 weeks, or up to 8 weeks under accelerated storage conditions. In some such embodiments, the terminally sterilized hydromorphone hydrochloride liquid formulation packaged in a multi-dose vial has a pH of about 3.6, about 3.7, about 3.8, about 3.9, or about 4.0 after storage for up to 2 weeks, up to 4 weeks, or up to 8 weeks under accelerated storage conditions.

In certain embodiments, the pH of the terminally sterilized hydromorphone hydrochloride liquid formulation packaged in a multi-dose vial does not materially change over time under accelerated storage conditions.

In certain embodiments, the terminally sterilized hydromorphone hydrochloride liquid formulation packaged in a multi-dose vial retains at least 90%, alternatively at least 91%, alternatively at least 92%, alternatively at least 93%, alternatively at least 94%, alternatively at least 95%, alternatively at least 96%, alternatively at least 97%, or alternatively at least 98% of the hydromorphone hydrochloride in the liquid formulation after storage for up to 2 weeks, up to 4 weeks, or up to 8 weeks under accelerated storage conditions as determined by HPLC. In some such embodiments, the terminally sterilized hydromorphone hydrochloride liquid formulation packaged in a multi-dose vial retains from about 90% to about 110%, alternatively from about 95% to about 105%, of the hydromorphone hydrochloride in the liquid formulation after storage for up to 2 weeks, up to 4 weeks, or up to 8 weeks under accelerated storage conditions as determined by HPLC.

In some such embodiments, the amount of hydromorphone hydrochloride retained following storage is with reference to the hydromorphone hydrochloride concentration prior to storage. In some such embodiments, the hydromorphone hydrochloride concentration prior to storage is from about 0.5 mg/mL to about 10.0 mg/mL, alternatively from about 1.0 mg/mL to about 5.0 mg/mL, or alternatively from about 1.5 mg/mL to about 2.5 mg/mL. In some such embodiments, the hydromorphone hydrochloride concentration prior to storage is 2.0 mg/mL. In some such embodiments, the amount of hydromorphone hydrochloride retained following storage is with reference to a product label claim. In some such embodiments, the product label claim for hydromorphone hydrochloride is from about 0.5 mg/mL to about 10.0 mg/mL, alternatively from about 1.0 mg/mL to about 5.0 mg/mL, or alternatively from about 1.5 mg/mL to about 2.5 mg/mL. In some such embodiments, the product label claim for hydromorphone hydrochloride is 2.0 mg/mL.

In certain embodiments, the amount of hydromorphone hydrochloride in the terminally sterilized hydromorphone hydrochloride liquid formulation packaged in a multi-dose vial does not materially change over time under accelerated storage conditions.

In certain embodiments, the terminally sterilized hydromorphone hydrochloride liquid formulation packaged in a multi-dose vial contains not more than 1.0%, not more than 0.9%, not more than 0.8%, not more than 0.7%, not more than 0.6%, not more than 0.5%, not more than 0.4%, not more than 0.3%, not more than 0.2%, or not more than 0.1% of any individual specified or unspecified related substance (e.g., degradation products such as 2,2'-bishydromorphone, hydromorphone N-oxide, 4-hydroxybenzoic acid, and 7-hydroperoxyl hydromorphone and 7-hydroxyl hydromorphone (the 7-substituted hydromorphone compounds can be considered together)) after storage for up to 2 weeks, up to 4 weeks, or up to 8 weeks under accelerated storage conditions as determined by HPLC.

In certain embodiments, the terminally sterilized hydromorphone hydrochloride liquid formulation packaged in a multi-dose vial contains not more than 4.0%, not more than 3.0%, not more than 2.0%, not more than 1.0%, or not more than 0.5% total related substances after storage for up to 2 weeks, up to 4 weeks, or up to 8 weeks under accelerated storage conditions as determined by HPLC.

In some such embodiments, the terminally sterilized hydromorphone hydrochloride liquid formulation packaged in a multi-dose vial contains not more than 0.25%, not more than 0.20%, not more than 0.15%, or not more than 0.10% w/w of total related substances after storage for 2, 4, or 8 weeks under accelerated storage conditions (e.g., 40° C.±2° C. and 75% RH±5% RH) as determined by HPLC. In some such embodiments, the liquid formulation retains at least 95%, preferably at least 98%, and more preferably at least 99% w/w of the hydromorphone hydrocholoride after storage for 2, 4, or 8 weeks under accelerated storage conditions as determined by HPLC.

In certain embodiments, the terminally sterilized hydromorphone hydrochloride liquid formulation packaged in a multi-dose vial has a pH in the range of about 3.5 to about 5.5, alternatively, from about 3.5 to 4.5, or alternatively from about 3.8 to about 4.2 after storage for up to 2 weeks, up to 4 weeks, or up to 8 weeks under stress storage conditions. In some such embodiments, the terminally sterilized hydromorphone hydrochloride liquid formulation packaged in a multi-dose vial has a pH of about 3.6, about 3.7, about 3.8, about 3.9, or about 4.0 after storage for up to 2 weeks, up to 4 weeks, or up to 8 weeks under stress storage conditions.

In certain embodiments, the pH of the terminally sterilized hydromorphone hydrochloride liquid formulation packaged in a multi-dose vial does not materially change over time under stress storage conditions.

In certain embodiments, the terminally sterilized hydromorphone hydrochloride liquid formulation packaged in a multi-dose vial retains at least 90%, alternatively at least 91%, alternatively at least 92%, alternatively at least 93%, alternatively at least 94%, alternatively at least 95%, alternatively at least 96%, alternatively at least 97%, or alternatively at least 98% of the hydromorphone hydrochloride in the liquid formulation after storage for up to 2 weeks, 4 weeks, or 8 weeks under stress storage conditions as determined by HPLC. In some such embodiments, the terminally sterilized hydromorphone hydrochloride liquid formulation packaged in a multi-dose vial retains from about 90% to about 110%, alternatively from about 95% to about 105%, of the hydromorphone hydrochloride in the liquid formulation after storage for up to 2 weeks, 4 weeks, or 8 weeks under stress storage conditions as determined by HPLC.

In some such embodiments, the amount of hydromorphone hydrochloride retained following storage is with reference to the hydromorphone hydrochloride concentration prior to storage. In some such embodiments, the hydromorphone hydrochloride concentration prior to storage is from about 0.5 mg/mL to about 10.0 mg/mL, alternatively from about 1.0 mg/mL to about 5.0 mg/mL, or alternatively from about 1.5 mg/mL to about 2.5 mg/mL. In some such embodiments, the hydromorphone hydrochloride concentration prior to storage is 2.0 mg/mL. In some such embodiments, the amount of hydromorphone hydrochloride retained following storage is with reference to a product label claim. In some such embodiments, the product label claim for hydromorphone hydrochloride is from about 0.5 mg/mL to about 10.0 mg/mL, alternatively from about 1.0 mg/mL to about 5.0 mg/mL, or alternatively from about 1.5 mg/mL to about 2.5 mg/mL. In some such embodiments, the product label claim for hydromorphone hydrochloride is 2.0 mg/mL.

In certain embodiments, the amount of hydromorphone hydrochloride in the terminally sterilized hydromorphone hydrochloride liquid formulation packaged in a multi-dose vial does not materially change over time under stress storage conditions.

In certain embodiments, the terminally sterilized hydromorphone hydrochloride liquid formulation packaged in a multi-dose vial contains not more than 1.0%, not more than 0.9%, not more than 0.8%, not more than 0.7%, not more than 0.6%, not more than 0.5%, not more than 0.4%, not more than 0.3%, or not more than 0.2% of any individual specified or unspecified related substance (e.g., degradation products such as 2,2'-bishydromorphone, hydromorphone N-oxide, and 7-hydroperoxyl hydromorphone and 7-hydroxyl hydromorphone (the 7-substituted hydromorphone compounds can be considered together)) after storage for up to 2 weeks, up to 4 weeks, or up to 8 weeks under stress storage conditions as determined by HPLC.

In certain embodiments, the terminally sterilized hydromorphone hydrochloride liquid formulation packaged in a multi-dose vial contains not more than 4.0%, not more than 3.0%, not more than 2.0%, not more than 1.0%, or not more than 0.5% total related substances after storage for up to 2 weeks, up to 4 weeks, or up to 8 weeks under stress storage conditions as determined by HPLC.

In certain embodiments, the terminally sterilized hydromorphone hydrochloride liquid formulation packaged in a multi-dose vial contains not more than 0.50%, not more than 0.40%, not more than 0.30%, not more than 0.25%, not more than 0.20%, or not more than 0.15% w/w of total related substances after storage for 8 weeks under stress storage conditions (e.g., 50° C.) as determined by HPLC. In some such embodiments, the liquid formulation retains at least 95%, preferably at least 98%, and more preferably at least 99% w/w of the hydromorphone hydrocholoride after storage for 8 weeks under stress storage conditions as determined by HPLC.

In certain embodiments, the terminally sterilized hydromorphone hydrochloride liquid formulation packaged in a multi-dose vial contains not more than 0.25%, not more than 0.20%, or not more than 0.15% of 7-hydroperoxyl hydromorphone and 7-hydroxyl hydromorphone (the 7-substituted hydromorphone compounds are considered together)

after storage for 8 weeks under stress storage conditions (e.g., 50° C.) as determined by HPLC. In some such embodiments, the liquid formulation retains at least 95%, preferably at least 98%, and more preferably at least 99% w/w of the hydromorphone hydrocholoride after storage for 8 weeks under stress storage conditions as determined by HPLC.

In some such embodiments, the pH of the liquid formulation after storage at 50° C. for 8 weeks is in the range of about 3.5 to 4.5, alternatively from about 3.6 to 4.4, or alternatively from about 3.7 to about 4.3.

H. METHODS OF USE

In at least one aspect, this disclosure provides methods for the management of pain using the liquid formulations described herein. Liquid formulations comprising hydromorphone or a pharmaceutically acceptable salt thereof may be used for the management of pain and, in particular, for the management of pain severe enough to require an opioid analgesic and for which alternate treatments are inadequate. Liquid formulations described herein may preferably be parenterally administered to a subject in need thereof. In particular, liquid formulations described herein may be subcutaneously, intramuscularly, or intravenously administered to a subject in need thereof.

Thus, in certain embodiments, the methods comprise parenterally administering to a subject in need of management of pain the terminally sterilized hydromorphone hydrochloride liquid formulations described herein. In some such embodiments, the methods comprise subcutaneously administering to a subject in need of management of pain the terminally sterilized hydromorphone hydrochloride liquid formulations described herein. In some such embodiments, the methods comprise intramuscularly administering to a subject in need of management of pain the terminally sterilized hydromorphone hydrochloride liquid formulations described herein. In some such embodiments, the methods comprise intravenously administering to a subject in need of management of pain the terminally sterilized hydromorphone hydrochloride liquid formulations described herein.

In certain embodiments, the subject is a human.

The liquid formulations, methods, and uses described herein will be better understood by reference to the following exemplary embodiments and examples, which are included as an illustration of and not a limitation upon the scope of the invention.

I. EXAMPLES

In order to demonstrate the practice of the subject matter disclosed herein, the following examples have been prepared and tested. The examples should not, however, be viewed as limiting the scope of the invention.

Example 1: Terminal Sterilization Feasibility

This study characterized the impact of terminal sterilization on a 2.0 mg/mL bulk solution of hydromorphone hydrochloride. The drug product was prepared and analyzed to investigate the suitability of the formulation and container closure system.

The batch was prepared using the formulation in Table 3 according to the procedure described herein.

TABLE 3

Formulation for Hydromorphone Hydrochloride 2 mg/mL

| Ingredient | Function | Amount per mL |
|---|---|---|
| Hydromorphone Hydrochloride, USP | Active Ingredient | 2 mg |
| Edetate Disodium, USP | Stabilizing Agent | 0.5 mg |
| Methylparaben, NF | Preservative | 1.8 mg |
| Propylparaben, NF | Preservative | 0.2 mg |
| Sodium Hydroxide, NF | pH adjustment | pH adjustment |
| Hydrochloric Acid, NF | pH adjustment | pH adjustment |
| Water for Injection | Aqueous Vehicle | q.s. to 1 ml |

Clear glass vials were filled at 8% oxygen headspace then terminally sterilized for 0, 15, 20, or 30 minutes at 121° C.±2° C.

The results of the analysis are presented in Table 4.

TABLE 4

Terminal Sterilization Results for Hydromorphone Hydrochloride

| | | Terminal Sterilization (min) | | | |
|---|---|---|---|---|---|
| | Test | 0 | 15 | 20 | 30 |
| | pH | 4.81 | 4.87 | 4.82 | 4.83 |
| Assay (%) | Hydromorphone | 102.0 | 101.5 | 101.5 | 100.6 |
| Parabens Degradant | 4-hydroxybenzoic acid | ND | ND | ND | ND |
| Related Substances | 7-hydroperoxyl & 7-hydroxyl hydromorphone | <LOQ | <LOQ | 0.05 | 0.06 |
| | 2,2'-bishydromorphone | <LOQ | <LOQ | <LOQ | <LOQ |

No significant degradation was seen in all assays when terminally sterilized. A slight increase in 7-hydroperoxyl & 7-hydroxyl hydromorphone was observed with sterilization however the values were still well within the release specification (NMT 0.2%). These results indicated that the drug product is capable of withstanding terminal sterilization.

Example 2: Impact of Initial pH on Stability

The effect of initial pH during the terminal sterilization process on the product was characterized in this study. Samples of pH 3.6, pH 4.5, and pH 5.4 were exposed to either 0, 15, or 35 minutes terminal sterilization cycles at 121° C.±2° C. Vials were filled under 8% oxygen headspace into the container.

Samples were placed on long-term (25±2° C. and 60±5% Relative Humidity (RH)), accelerated (40±2° C. and 75±5% RH), and stress (50° C.) storage conditions in upright and inverted orientations.

Samples were assessed by hydromorphone hydrochloride assay at 0, 2, 4, and 8 weeks. Appearance, pH, and individual related substances were also assessed.

Tables 5-7 show stability under long-term storage conditions over time.

Tables 8-10 show stability under accelerated storage conditions over time.

Tables 11-13 show stability under stress storage conditions over time.

TABLE 5

(initial pH 3.6, storage at 25 ± 2° C. and 60 ± 5% RH).

| Test | Time Point (weeks) | | | | | | | | |
|---|---|---|---|---|---|---|---|---|---|
| | Non-TS | | | | | | TS = 15 minutes | | |
| | 0 | 2 | 4 | 8 | 12 | 24 | 0 | 2 | 4 |
| pH | 3.6 | 3.8 | 3.7 | 3.7 | 3.8 | 3.7 | 3.7 | 3.8 | 3.7 |
| Appearance | Clear, colorless, and free of visible particulates | | | | | | | | |
| Hydromorphone | 99.6 | 100.6 | 102.0 | 100.5 | 102.4 | 100.4 | 100.5 | 100.3 | 98.8 |
| 2,2-bishydromorphone | <LOQ | <LOQ | <LOQ | <LOQ | N.D. | 0.07 | <LOQ | <LOQ | <LOQ |
| Hydromorphone N-oxide | N.D. | N.D. | N.D. | N.D. | N.D. | ND | N.D. | N.D. | N.D. |
| 4-hydroxybenzoic acid | <LOQ | <LOQ | <LOQ | <LOQ | <LOQ | 0.10 | <LOQ | <LOQ | <LOQ |
| 7-hydroperoxyl & 7-hydroxyl hydromorphone | <LOQ | <LOQ | <LOQ | <LOQ | <LOQ | <LOQ | <LOQ | <LOQ | 0.05 |
| Highest individual unspecified degradant | N.D. | N.D. | <LOQ | 0.07 | <LOQ | ND | N.D. | N.D. | <LOQ |
| Total degradation products | <LOQ | <LOQ | <LOQ | 0.07 | <LOQ | 0.07 | <LOQ | <LOQ | 0.05 |

| Test | Time Point (weeks) | | | | | | | | |
|---|---|---|---|---|---|---|---|---|---|
| | TS = 15 minutes | | | TS = 35 minutes | | | | | |
| | 8 | 12 | 24 | 0 | 2 | 4 | 8 | 12 | 24 |
| pH | 3.7 | 3.8 | 3.7 | 3.7 | 3.7 | 3.7 | 3.7 | 3.8 | 3.7 |
| Appearance | Clear, colorless, and free of visible particulates | | | | | | | | |
| Hydromorphone | 100.4 | 102.8 | 100.7 | 101.5 | 100.6 | 101.5 | 100.3 | 103.2 | 100.3 |
| 2,2-bishydromorphone | <LOQ | N.D. | <LOQ | <LOQ | <LOQ | <LOQ | <LOQ | N.D. | <LOQ |
| Hydromorphone N-oxide | N.D. | N.D. | N.D. | N.D. | N.D. | N.D. | N.D. | N.D. | N.D. |
| 4-hydroxybenzoic acid | 0.05 | 0.06 | 0.11 | 0.05 | 0.06 | 0.06 | 0.06 | 0.08 | 0.13 |
| 7-hydroperoxyl & 7-hydroxyl hydromorphone | <LOQ | <LOQ | <LOQ | <LOQ | <LOQ | <LOQ | <LOQ | <LOQ | <LOQ |
| Highest individual unspecified degradant | 0.05 | <LOQ | 0.06 | N.D. | N.D. | N.D. | <LOQ | <LOQ | 0.07 |
| Total degradation products | 0.05 | <LOQ | 0.06 | <LOQ | <LOQ | <LOQ | <LOQ | <LOQ | 0.07 |

LOQ = limit of quantitation;
N.D. = none detected

TABLE 6

(initial pH 4.5, storage at 25 ± 2° C. and 60 ± 5% RH).

| Test | Time Point (weeks) | | | | | | | | |
|---|---|---|---|---|---|---|---|---|---|
| | Non-TS | | | | | | TS = 15 minutes | | |
| | 0 | 2 | 4 | 8 | 12 | 24 | 0 | 2 | 4 |
| pH | 4.5 | 4.6 | 4.6 | 4.5 | 4.6 | 4.6 | 4.6 | 4.7 | 4.7 |
| Appearance | Clear, colorless, and free of visible particulates | | | | | | | | |
| Hydromorphone | 100.8 | 99.7 | 100.0 | 99.9 | 101.2 | 98.8 | 101.3 | 99.8 | 100.6 |
| 2,2-bishydromorphone | <LOQ | <LOQ | <LOQ | <LOQ | N.D. | <LOQ | <LOQ | <LOQ | <LOQ |
| Hydromorphone N-oxide | N.D. | N.D. | N.D. | N.D. | N.D. | N.D. | N.D. | N.D. | N.D. |
| 4-hydroxybenzoic acid | N.D. | <LOQ | N.D. | <LOQ | <LOQ | <LOQ | <LOQ | <LOQ | <LOQ |
| 7-hydroperoxyl & 7-hydroxyl hydromorphone | <LOQ | <LOQ | 0.06 | <LOQ | <LOQ | 0.08 | <LOQ | <LOQ | <LOQ |

TABLE 6-continued (initial pH 4.5, storage at 25 ± 2° C. and 60 ± 5% RH).

| | | | | | | | | | |
|---|---|---|---|---|---|---|---|---|---|
| Highest individual unspecified degradant | N.D. | N.D. | N.D. | 0.07 | <LOQ | <LOQ | N.D. | N.D. | N.D. |
| Total degradation products | <LOQ | <LOQ | 0.06 | 0.07 | <LOQ | 0.08 | <LOQ | <LOQ | <LOQ |

| | Time Point (weeks) | | | | | | | | |
|---|---|---|---|---|---|---|---|---|---|
| | TS = 15 minutes | | | TS = 35 minutes | | | | | |
| Test | 8 | 12 | 24 | 0 | 2 | 4 | 8 | 12 | 24 |
| pH | 4.6 | 4.7 | 4.6 | 4.6 | 4.6 | 4.6 | 4.6 | 4.7 | 4.6 |
| Appearance | Clear, colorless, and free of visible particulates | | | | | | | | |
| Hydromorphone | 99.9 | 102.4 | 100.0 | 101.3 | 99.6 | 102.6 | 99.7 | 102.3 | 100.5 |
| 2,2-bishydromorphone | <LOQ | N.D. | <LOQ | <LOQ | <LOQ | <LOQ | <LOQ | N.D. | <LOQ |
| Hydromorphone N-oxide | N.D. | N.D. | N.D. | N.D. | N.D. | N.D. | N.D. | N.D. | N.D. |
| 4-hydroxybenzoic acid | <LOQ | <LOQ | 0.08 | 0.006 | 0.06 | 0.08 | 0.06 | 0.07 | 0.12 |
| 7-hydroperoxyl & 7-hydroxyl hydromorphone | 0.06 | <LOQ | 0.11 | <LOQ | <LOQ | 0.08 | 0.07 | 0.05 | 0.12 |
| Highest individual unspecified degradant | <LOQ | <LOQ | 0.07 | <LOQ | N.D. | <LOQ | N.D. | <LOQ | 0.05 |
| Total degradation products | 0.06 | <LOQ | 0.18 | <LOQ | <LOQ | 0.08 | 0.07 | 0.05 | 0.17 |

LOQ = limit of quantitation;
N.D. = none detected

TABLE 7

(initial pH 5.4, storage at 25 ± 2° C. and 60 ± 5% RH).

| | Time Point (weeks) | | | | | | | | |
|---|---|---|---|---|---|---|---|---|---|
| | Non-TS | | | | | | TS = 15 minutes | | |
| Test | 0 | 2 | 4 | 8 | 12 | 24 | 0 | 2 | 4 |
| pH | 5.4 | 5.5 | 5.4 | 5.4 | 5.5 | 5.4 | 5.4 | 5.5 | 5.4 |
| Appearance | Clear, colorless, and free of visible particulates | | | | | | | | |
| Hydromorphone | 100.4 | 100.4 | 104.3 | 100.4 | 102.4 | 99.6 | 103.5 | 100.9 | 102.1 |
| 2,2-bishydromorphone | <LOQ | <LOQ | <LOQ | <LOQ | N.D. | <LOQ | <LOQ | <LOQ | <LOQ |
| Hydromorphone N-oxide | N.D. | N.D. | N.D. | N.D. | N.D. | N.D. | N.D. | N.D. | N.D. |
| 4-hydroxybenzoic acid | <LOQ | <LOQ | <LOQ | <LOQ | 0.05 | 0.13 | 0.07 | 0.07 | 0.09 |
| 7-hydroperoxyl & 7-hydroxyl hydromorphone | <LOQ | <LOQ | 0.06 | 0.06 | <LOQ | 0.11 | <LOQ | 0.05 | 0.10 |
| Highest individual unspecified degradant | N.D. | N.D. | N.D. | 0.07 | <LOQ | <LOQ | N.D. | N.D. | N.D. |
| Total degradation products | <LOQ | <LOQ | 0.06 | 0.13 | <LOQ | 0.11 | <LOQ | 0.05 | 0.10 |

| | Time Point (weeks) | | | | | | | | |
|---|---|---|---|---|---|---|---|---|---|
| | TS = 15 minutes | | | TS = 35 minutes | | | | | |
| Test | 8 | 12 | 24 | 0 | 2 | 4 | 8 | 12 | 24 |
| pH | 5.4 | 5.5 | 5.4 | 5.4 | 5.4 | 5.4 | 5.3 | 5.5 | 5.4 |
| Appearance | Clear, colorless, and free of visible particulates | | | | | | | | |
| Hydromorphone | 101.1 | 102.2 | 99.6 | 102.4 | 100.0 | 103.4 | 100.7 | 102.6 | 100.4 |
| 2,2-bishydromorphone | <LOQ | N.D. | <LOQ | <LOQ | <LOQ | <LOQ | <LOQ | N.D. | <LOQ |
| Hydromorphone N-oxide | N.D. | N.D. | N.D. | N.D. | N.D. | N.D. | N.D. | N.D. | N.D. |
| 4-hydroxybenzoic acid | 0.08 | 0.09 | 0.19 | 0.12 | 0.11 | 0.13 | 0.11 | 0.14 | 0.26 |

TABLE 7-continued

| (initial pH 5.4, storage at 25 ± 2° C. and 60 ± 5% RH). | | | | | | | | | |
|---|---|---|---|---|---|---|---|---|---|
| 7-hydroperoxyl & 7-hydroxyl hydromorphone | 0.08 | 0.06 | 0.13 | <LOQ | 0.06 | 0.12 | 0.10 | 0.06 | 0.14 |
| Highest individual unspecified degradant | <LOQ | <LOQ | <LOQ | <LOQ | <LOQ | <LOQ | <LOQ | <LOQ | 0.05 |
| Total degradation products | 0.08 | 0.06 | 0.13 | <LOQ | 0.06 | 0.12 | 0.10 | 0.06 | 0.19 |

LOQ = limit of quantitation;
N.D. = none detected

TABLE 8

(initial pH 3.6, storage at 40 ± 2° C. and 75 ± 5% RH).

| | Time Point (weeks) | | | | | | | | |
|---|---|---|---|---|---|---|---|---|---|
| | Non-TS | | | | | | TS = 15 minutes | | |
| Test | 0 | 2 | 4 | 8 | 12 | 24 | 0 | 2 | 4 |
| pH | 3.6 | 3.7 | 3.8 | 3.7 | 3.8 | 3.8 | 3.7 | 3.7 | 3.6 |
| Appearance | Clear, colorless, and free of visible particulates | | | | | | | | |
| Hydromorphone | 99.6 | 100.4 | 102.6 | 99.6 | 104.3 | 100.7 | 100.5 | 101.1 | 103.5 |
| 2,2-bishydromorphone | <LOQ | <LOQ | <LOQ | <LOQ | N.D. | 0.05 | <LOQ | <LOQ | <LOQ |
| Hydromorphone N-oxide | N.D. | N.D. | N.D. | N.D. | N.D. | N.D. | N.D. | N.D. | N.D. |
| 4-hydroxybenzoic acid | <LOQ | <LOQ | 0.07 | 0.09 | 0.16 | 0.33 | <LOQ | 0.06 | 0.09 |
| 7-hydroperoxyl & 7-hydroxyl hydromorphone | <LOQ | <LOQ | <LOQ | <LOQ | <LOQ | 0.07 | <LOQ | <LOQ | 0.05 |
| Highest individual unspecified degradant | N.D. | N.D. | N.D. | 0.06 | <LOQ | 0.06 | N.D. | N.D. | N.D. |
| Total degradation products | <LOQ | <LOQ | <LOQ | 0.06 | <LOQ | 0.18 | <LOQ | <LOQ | 0.05 |

| | Time Point (weeks) | | | | | | | | |
|---|---|---|---|---|---|---|---|---|---|
| | TS = 15 minutes | | | TS = 35 minutes | | | | | |
| Test | 8 | 12 | 24 | 0 | 2 | 4 | 8 | 12 | 24 |
| pH | 3.7 | 3.8 | 3.8 | 3.7 | 3.7 | 3.7 | 3.7 | 3.8 | 3.8 |
| Appearance | Clear, colorless, and free of visible particulates | | | | | | | | |
| Hydromorphone | 100.2 | 102.7 | 106.3 | 101.5 | 99.8 | 101.7 | 100.8 | 101.8 | 100.1 |
| 2,2-bishydromorphone | <LOQ | N.D. | 0.06 | <LOQ | <LOQ | <LOQ | <LOQ | N.D. | 0.06 |
| Hydromorphone N-oxide | N.D. | N.D. | N.D. | N.D. | N.D. | N.D. | N.D. | N.D. | N.D. |
| 4-hydroxybenzoic acid | 0.11 | 0.16 | 0.36 | 0.05 | 0.07 | 0.10 | 0.12 | 0.17 | 0.36 |
| 7-hydroperoxyl & 7-hydroxyl hydromorphone | 0.06 | <LOQ | 0.08 | <LOQ | <LOQ | 0.07 | 0.06 | <LOQ | 0.08 |
| Highest individual unspecified degradant | 0.05 | <LOQ | <LOQ | N.D. | <LOQ | <LOQ | <LOQ | <LOQ | <LOQ |
| Total degradation products | 0.11 | <LOQ | 0.14 | <LOQ | <LOQ | 0.07 | 0.06 | <LOQ | 0.14 |

LOQ = limit of quantitation;
N.D. = none detected

TABLE 9

(initial pH 4.5, storage at 40 ± 2° C. and 75 ± 5% RH).

| | Time Point (weeks) | | | | | | | | |
|---|---|---|---|---|---|---|---|---|---|
| | Non-TS | | | | | | TS = 15 minutes | | |
| Test | 0 | 2 | 4 | 8 | 12 | 24 | 0 | 2 | 4 |
| pH | 4.5 | 4.5 | 4.7 | 4.4 | 4.7 | 4.7 | 4.6 | 4.7 | 4.6 |
| Appearance | Clear, colorless, and free of visible particulates | | | | | | | | |
| Hydromorphone | 100.8 | 98.8 | 101.1 | 100.8 | 101.8 | 99.6 | 101.3 | 96.6 | 99.5 |
| 2,2-bishydromorphone | <LOQ | <LOQ | <LOQ | <LOQ | N.D. | <LOQ | <LOQ | <LOQ | <LOQ |
| Hydromorphone N-oxide | N.D. | N.D. | N.D. | N.D. | N.D. | N.D. | N.D. | N.D. | N.D. |
| 4-hydroxybenzoic acid | N.D. | <LOQ | <LOQ | 0.05 | 0.08 | 0.21 | <LOQ | 0.05 | 0.06 |
| 7-hydroperoxyl & 7-hydroxyl hydromorphone | <LOQ | <LOQ | 0.10 | 0.10 | 0.09 | 0.21 | <LOQ | <LOQ | 0.11 |
| Highest individual unspecified degradant | N.D. | N.D. | <LOQ | 0.06 | <LOQ | 0.08 | N.D. | <LOQ | <LOQ |
| Total degradation products | <LOQ | <LOQ | 0.10 | 0.16 | 0.09 | 0.29 | <LOQ | <LOQ | 0.11 |

| | Time Point (weeks) | | | | | | | | |
|---|---|---|---|---|---|---|---|---|---|
| | TS = 15 minutes | | | TS = 35 minutes | | | | | |
| Test | 8 | 12 | 24 | 0 | 2 | 4 | 8 | 12 | 24 |
| pH | 4.5 | 4.7 | 4.6 | 4.6 | 4.7 | 4.6 | 4.5 | 4.7 | 4.6 |
| Appearance | Clear, colorless, and free of visible particulates | | | | | | | | |
| Hydromorphone | 100.4 | 100.8 | 99.3 | 101.3 | 97.6 | 101.2 | 100.7 | 101.7 | 99.2 |
| 2,2-bishydromorphone | <LOQ | N.D. | <LOQ | <LOQ | <LOQ | <LOQ | <LOQ | N.D. | <LOQ |
| Hydromorphone N-oxide | N.D. | N.D. | N.D. | N.D. | N.D. | N.D. | N.D. | N.D. | N.D. |
| 4-hydroxybenzoic acid | 0.07 | 0.09 | 0.23 | 0.06 | 0.08 | 0.10 | 0.09 | 0.12 | 0.28 |
| 7-hydroperoxyl & 7-hydroxyl hydromorphone | 0.12 | 0.12 | 0.22 | <LOQ | LOQ | 0.10 | 0.14 | 0.13 | 0.22 |
| Highest individual unspecified degradant | <LOQ | <LOQ | 0.08 | <LOQ | N.D. | N.D. | N.D. | <LOQ | 0.08 |
| Total degradation products | 0.12 | 0.12 | 0.30 | <LOQ | <LOQ | 0.10 | 0.14 | 0.13 | 0.30 |

LOQ = limit of quantitation;
N.D. = none detected

TABLE 10

(initial pH 5.4, storage at 40 ± 2° C. and 75 ± 5% RH).

| | Time Point (weeks) | | | | | | | | |
|---|---|---|---|---|---|---|---|---|---|
| | Non-TS | | | | | | TS = 15 minutes | | |
| Test | 0 | 2 | 4 | 8 | 12 | 24 | 0 | 2 | 4 |
| pH | 5.4 | 5.4 | 5.4 | 5.2 | 5.5 | 5.3 | 5.4 | 5.4 | 5.5 |
| Appearance | Clear, colorless, and free of visible particulates | | | | | | | | |
| Hydromorphone | 100.4 | 98.9 | 101.0 | 99.5 | 101.4 | 98.9 | 103.5 | 99.8 | 100.4 |
| 2,2-bishydromorphone | <LOQ | <LOQ | <LOQ | <LOQ | N.D. | <LOQ | <LOQ | <LOQ | <LOQ |
| Hydromorphone N-oxide | N.D. | N.D. | N.D. | N.D. | N.D. | N.D. | N.D. | N.D. | N.D. |
| 4-hydroxybenzoic acid | <LOQ | 0.07 | 0.11 | 0.12 | 0.19 | 0.66 | 0.07 | 0.12 | 0.17 |
| 7-hydroperoxyl & 7-hydroxyl hydromorphone | <LOQ | 0.07 | 0.13 | 0.16 | 0.14 | 0.28 | <LOQ | 0.09 | 0.17 |

TABLE 10-continued (initial pH 5.4, storage at 40 ± 2° C. and 75 ± 5% RH).

| | | | | | | | | | |
|---|---|---|---|---|---|---|---|---|---|
| Highest individual unspecified degradant | N.D. | N.D. | N.D. | <LOQ | 0.07 | 0.15 | N.D. | <LOQ | <LOQ |
| Total degradation products | <LOQ | 0.07 | 0.13 | 0.16 | 0.21 | 0.50 | <LOQ | 0.09 | 0.17 |

| | Time Point (weeks) | | | | | | | | |
|---|---|---|---|---|---|---|---|---|---|
| | TS = 15 minutes | | | TS = 35 minutes | | | | | |
| Test | 8 | 12 | 24 | 0 | 2 | 4 | 8 | 12 | 24 |
| pH | 5.2 | 5.4 | 5.2 | 5.4 | 5.4 | 5.4 | 5.3 | 5.4 | 5.2 |
| Appearance | Clear, colorless, and free of visible particulates | | | | | | | | |
| Hydromorphone | 100.6 | 102.2 | 99.1 | 102.4 | 99.3 | 102.3 | 101.0 | 101.2 | 95.9 |
| 2,2-bishydromorphone | <LOQ | N.D. | <LOQ | <LOQ | <LOQ | <LOQ | <LOQ | N.D. | <LOQ |
| Hydromorphone N-oxide | N.D. | N.D. | <LOQ | N.D. | N.D. | N.D. | N.D. | N.D. | <LOQ |
| 4-hydroxybenzoic acid | 0.17 | 0.25 | 0.73 | 0.12 | 0.16 | 0.23 | 0.20 | 0.28 | 0.76 |
| 7-hydroperoxyl & 7-hydroxyl hydromorphone | 0.17 | 0.20 | 0.29 | <LOQ | 0.10 | 0.15 | 0.19 | 0.20 | 0.28 |
| Highest individual unspecified degradant | <LOQ | 0.09 | 0.16 | <LOQ | <LOQ | N.D. | 0.06 | 0.13 | 0.17 |
| Total degradation products | 0.17 | 0.29 | 0.53 | <LOQ | 0.10 | 0.15 | 0.25 | 0.33 | 0.52 |

LOQ = limit of quantitation;
N.D. = none detected

TABLE 11

(initial pH 3.6, storage at 50° C.).

| | Time Point (weeks) | | | | | | | | | | | |
|---|---|---|---|---|---|---|---|---|---|---|---|---|
| | Non-TS | | | | TS = 15 minutes | | | | TS = 35 minutes | | | |
| Test | 0 | 2 | 4 | 8 | 0 | 2 | 4 | 8 | 0 | 2 | 4 | 8 |
| pH | 3.6 | 3.7 | 3.7 | 3.7 | 3.7 | 3.8 | 3.8 | 3.8 | 3.7 | 3.7 | 3.8 | 3.7 |
| Appearance | Clear, colorless, and free of visible particulates | | | | | | | | | | | |
| Hydromorphone | 99.6 | 99.7 | 103.4 | 100.0 | 100.5 | 99.4 | 105.3 | 100.7 | 101.5 | 98.9 | 103.4 | 99.6 |
| 2,2-bishydromorphone | <LOQ | <LOQ | <LOQ | <LOQ | <LOQ | <LOQ | <LOQ | <LOQ | <LOQ | <LOQ | N.D. | <LOQ |
| Hydromorphone N-oxide | N.D. | N.D. | N.D. | N.D. | N.D. | N.D. | N.D. | N.D. | N.D. | N.D. | N.D. | N.D. |
| 4-hydroxybenzoic acid | <LOQ | 0.11 | 0.19 | 0.27 | <LOQ | 0.12 | 0.21 | 0.28 | 0.05 | 0.14 | 0.22 | 0.29 |
| 7-hydroperoxyl & 7-hydroxyl hydromorphone | <LOQ | <LOQ | 0.11 | 0.09 | <LOQ | 0.05 | 0.09 | 0.10 | <LOQ | 0.06 | 0.08 | 0.12 |
| Highest individual unspecified degradant | N.D. | N.D. | <LOQ | <LOQ | N.D. | N.D. | 0.05 | <LOQ | N.D. | N.D. | <LOQ | <LOQ |
| Total degradation products | <LOQ | <LOQ | 0.11 | 0.09 | <LOQ | 0.05 | 0.14 | 0.10 | <LOQ | 0.06 | 0.13 | 0.12 |

LOQ = limit of quantitation;
N.D. = none detected

TABLE 12

(initial pH 4.5, storage at 50° C.).

| | Time Point (weeks) | | | | | | | | | | | |
|---|---|---|---|---|---|---|---|---|---|---|---|---|
| | Non-TS | | | | TS = 15 minutes | | | | TS = 35 minutes | | | |
| Test | 0 | 2 | 4 | 8 | 0 | 2 | 4 | 8 | 0 | 2 | 4 | 8 |
| pH | 4.5 | 4.6 | 4.7 | 4.5 | 4.6 | 4.7 | 4.6 | 4.6 | 4.6 | 4.6 | 4.6 | 4.6 |
| Appearance | Clear, colorless, and free of visible particulates | | | | | | | | | | | |
| Hydromorphone | 100.8 | 99.1 | 113.2* | 98.4 | 101.3 | 99.6 | 103.3 | 99.1 | 101.3 | 99.3 | 99.6 | 99.0 |
| 2,2-bishydromorphone | <LOQ | <LOQ | N.D. | <LOQ | <LOQ | <LOQ | N.D. | <LOQ | <LOQ | <LOQ | N.D. | <LOQ |
| Hydromorphone N-oxide | N.D. | N.D. | N.D. | N.D. | N.D. | N.D. | N.D. | N.D. | N.D. | N.D. | N.D. | N.D. |
| 4-hydroxybenzoic acid | N.D. | <LOQ | 0.13 | 0.15 | <LOQ | 0.07 | 0.14 | 0.18 | 0.06 | 0.09 | 0.13 | 0.20 |

TABLE 12-continued (initial pH 4.5, storage at 50° C.).

| Test | Time Point (weeks) | | | | | | | | | | | |
|---|---|---|---|---|---|---|---|---|---|---|---|---|
| | Non-TS | | | | TS = 15 minutes | | | | TS = 35 minutes | | | |
| | 0 | 2 | 4 | 8 | 0 | 2 | 4 | 8 | 0 | 2 | 4 | 8 |
| 7-hydroperoxyl & 7-hydroxyl hydromorphone | <LOQ | 0.07 | 0.24 | 0.22 | <LOQ | 0.09 | 0.21 | 0.24 | <LOQ | 0.11 | 0.10 | 0.25 |
| Highest individual unspecified degradant | N.D. | N.D. | 0.05 | 0.05 | N.D. | N.D. | 0.08 | 0.06 | <LOQ | <LOQ | 0.05 | 0.06 |
| Total degradation products | <LOQ | 0.07 | 0.29 | 0.27 | <LOQ | 0.09 | 0.29 | 0.30 | 0.00 | 0.11 | 0.15 | 0.32 |

LOQ = limit of quantitation;
N.D. = none detected
*Out of specification, result disregarded as sample error

TABLE 13

(initial pH 5.4, storage at 50° C.).

| Test | Time Point (weeks) | | | | | | | | | | | |
|---|---|---|---|---|---|---|---|---|---|---|---|---|
| | Non-TS | | | | TS = 15 minutes | | | | TS = 35 minutes | | | |
| | 0 | 2 | 4 | 8 | 0 | 2 | 4 | 8 | 0 | 2 | 4 | 8 |
| pH | 5.4 | 5.3 | 5.3 | 5.1 | 5.4 | 5.3 | 5.3 | 5.0 | 5.4 | 5.4 | 5.3 | 5.1 |
| Appearance | Clear, colorless, and free of visible particulates | | | | | | | | | | | |
| Hydromorphone | 100.4 | 99.5 | 97.4 | 100.1 | 103.5 | 98.0 | 101.0 | 100.0 | 102.4 | 97.4 | 100.1 | 98.5 |
| 2,2-bishydromorphone | <LOQ | <LOQ | <LOQ | <LOQ | <LOQ | <LOQ | <LOQ | <LOQ | <LOQ | <LOQ | <LOQ | <LOQ |
| Hydromorphone N-oxide | N.D. | N.D. | N.D. | N.D. | N.D. | N.D. | N.D. | N.D. | N.D. | N.D. | N.D. | N.D. |
| 4-hydroxybenzoic acid | <LOQ | 0.12 | 0.28 | 0.37 | 0.07 | 0.16 | 0.34 | 0.40 | 0.12 | 0.20 | 0.32 | 0.41 |
| 7-hydroperoxyl & 7-hydroxyl hydromorphone | <LOQ | 0.11 | 0.27 | 0.26 | <LOQ | 0.14 | 0.28 | 0.27 | <LOQ | 0.14 | 0.18 | 0.30 |
| Highest individual unspecified degradant | N.D. | <LOQ | 0.14 | 0.25 | N.D. | 0.06 | 0.18 | 0.27 | <LOQ | 0.08 | 0.28 | 0.32 |
| Total degradation products | <LOQ | 0.11 | 0.41 | 0.59 | <LOQ | 0.20 | 0.46 | 0.68 | <LOQ | 0.22 | 0.46 | 0.80 |

LOQ = limit of quantitation;
N.D. = none detected

Hydromorphone assay was very stable with values not less than 98% under 25±2° C./60±5% RH storage and not less than 96% under 40±2° C./75±5% RH storage for 24 weeks.

Degradants were more variable across the samples. 4-hydroxybenzoic acid and 7-hydroperoxyl & 7-hydroxyl hydromorphone degradants showed the largest increases throughout stability testing.

The 7-hydroperoxyl & 7-hydroxyl hydromorphone degradants and total degradants showed moderate increases over time with larger increases being observed within the first 4 weeks of storage.

The pH 3.6 solution was associated with lower total degradants, and 7-hydroperoxyl & 7-hydroxyl hydromorphone degradants as compared to the pH 4.5 solution. The pH 4.5 solution was associated with lower 4-hydroxybenzoic acid values as compared to the pH 3.6 solution. To balance these competing factors, a target initial pH of 3.9 to 4.1 is preferred.

From these results it was concluded that terminal sterilization is feasible for hydromorphone hydrochloride in a multi-dose vial, as comparable degradation profiles were achieved to non-TS samples. An exemplary TS cycle is 15 minutes at 121° C.±2° C.

Example 3: Stabilizing Agent Impact

This study evaluated the impact of an exemplary stabilizing agent, EDTA, on formulation stability in a container having a headspace comprising ambient air or an 8% oxygen headspace. Drug products were prepared as described in Table 3 according to the procedure described herein except that one formulation did not include EDTA.

Product was filled into the final container closure (20 mL vial) and terminally sterilized to an F0=15 min. A stability trial was initiated at Long-Term (25±2° C. and 60±5% Relative Humidity (RH)) and Accelerated (40±2° C. and 75±5% RH) storage conditions. The stability of the EDTA-free formulation in a container having 8% oxygen headspace is shown in Table 14. The stability of the EDTA-containing formulation in a container having 8% oxygen headspace is shown in Table 15. The stability of the EDTA-free formulation in a container having a headspace comprising ambient air is shown in Table 16. The stability of the EDTA-containing formulation in a container having a headspace comprising ambient air is shown in Table 17.

TABLE 14

EDTA Free Formulation Stability Ambient Headspace

| | | Time in Weeks | | | | | | | | | | |
|---|---|---|---|---|---|---|---|---|---|---|---|---|
| | | | Long-Term | | | | | Accelerated | | | | |
| | Test | Initial | 2 | 4 | 8 | 12 | 24 | 2 | 4 | 8 | 12 | 24 |
| | Appearance | Clear colorless solution free of visible particulates | | | | | | | | | | |
| | pH | 4.18 | 4.15 | 4.17 | 4.29 | 4.21 | 4.27 | 4.26 | 4.26 | 4.20 | 4.21 | 4.10 |
| Assay (%) | Hydromorphone | 102.9 | 101.3 | 99.5 | 101.2 | 103.3 | 103.9 | 101.3 | 99.9 | 103.1 | 102.9 | 102.8 |
| | Methylparaben | 103.5 | 101.8 | 99.9 | 99.6 | 99.9 | 102.4 | 101.6 | 100.0 | 101.4 | 99.4 | 100.9 |
| | Propylparaben | 102.5 | 100.4 | 98.8 | 96.3 | 92.1 | 97.7 | 99.0 | 97.2 | 96.6 | 90.3 | 93.3 |
| | EDTA | N/A | N/A | N/A | N/A | N/A | N/A | N/A | N/A | N/A | N/A | N/A |
| Degradation Products (%) | 4-Hydroxybenzoic Acid (Degradant of Parabens) | <LOQ | <LOQ | <LOQ | 0.05 | 0.07 | 0.09 | 0.05 | 0.07 | 0.11 | 0.17 | 0.28 |
| | 7-hydroperoxyl & 7-hydroxyl hydromorphone | 0.11 | 0.16 | 0.13 | 0.20 | 0.21 | 0.19 | 0.19 | 0.16 | 0.23 | 0.27 | 0.26 |
| | 2,2'-bishydromorphone | 0.18 | 0.18 | 0.18 | 0.18 | 0.18 | 0.18 | 0.19 | 0.17 | 0.19 | 0.19 | 0.19 |
| | Hydromorphone N-Oxide | ND | ND | ND | ND | ND | ND | ND | ND | ND | ND | ND |
| | Largest Individual Unspecified Degradant | 0.07 | 0.06 | 0.06 | 0.06 | 0.17 | 0.07 | 0.05 | 0.06 | 0.05 | 0.17 | 0.28 |
| | Total Degradation Products | 0.36 | 0.40 | 0.42 | 0.54 | 0.77 | 0.73 | 0.48 | 0.52 | 0.74 | 1.01 | 1.07 |

TABLE 15

EDTA Containing Formulation Stability Ambient Headspace

| | | Time in Weeks | | | | | | | | | | |
|---|---|---|---|---|---|---|---|---|---|---|---|---|
| | | | Long-Term | | | | | Accelerated | | | | |
| | Test | Initial | 2 | 4 | 8 | 12 | 24 | 2 | 4 | 8 | 12 | 24 |
| | Appearance | Clear colorless solution free of visible particulates | | | | | | | | | | |
| | pH | 4.06 | 4.06 | 4.13 | 4.15 | 4.15 | 4.27 | 4.15 | 4.05 | 4.10 | 4.11 | 4.11 |
| Assay (%) | Hydromorphone | 103.2 | 101.6 | 99.7 | 102.5 | 103.4 | 104.2 | 102.1 | 99.8 | 102.5 | 102.6 | 104.2 |
| | Methylparaben | 102.5 | 100.2 | 98.5 | 99.5 | 98.9 | 101.0 | 101.0 | 98.7 | 99.4 | 98.28 | 100.0 |
| | Propylparaben | 101.2 | 98.9 | 97.5 | 96.7 | 91.4 | 96.3 | 98.6 | 96.6 | 95.0 | 89.25 | 92.8 |
| | EDTA | 94.7 | 94.4 | 92.0 | 88.4 | 91.6 | 92.7 | 93.1 | 91.0 | 89.0 | 91.6 | 92.2 |
| Degradation Products (%) | 4-Hydroxybenzoic Acid (Degradant of Parabens) | <LOQ | <LOQ | <LOQ | 0.05 | 0.07 | 0.09 | 0.05 | 0.07 | 0.11 | 0.17 | 0.28 |
| | 7-hydroperoxyl & 7-hydroxyl hydromorphone | <LOQ | <LOQ | <LOQ | <LOQ | <LOQ | <LOQ | <LOQ | <LOQ | <LOQ | 0.08 | 0.07 |
| | 2,2'-bishydromorphone | <LOQ | <LOQ | ND | <LOQ | <LOQ | <LOQ | <LOQ | <LOQ | <LOQ | <LOQ | <LOQ |
| | Hydromorphone N-Oxide | ND | ND | ND | ND | ND | ND | ND | ND | ND | ND | ND |
| | Largest Individual Unspecified Degradant | <LOQ | 0.05 | 0.05 | 0.06 | 0.21 | 0.06 | 0.05 | 0.05 | 0.05 | 0.22 | 0.06 |
| | Total Degradation Products | <LOQ | 0.05 | 0.05 | 0.16 | 0.34 | 0.16 | 0.10 | 0.12 | 0.21 | 0.52 | 0.40 |

TABLE 16

EDTA Free Formulation Stability 8% Oxygen Headspace

| | | Time in Weeks | | | | | | | | | | |
|---|---|---|---|---|---|---|---|---|---|---|---|---|
| | | | Long-Term | | | | | Accelerated | | | | |
| | Test | Initial | 2 | 4 | 8 | 12 | 24 | 2 | 4 | 8 | 12 | 24 |
| | Appearance | Clear colorless solution free of visible particulates | | | | | | | | | | |
| | pH | 4.19 | 4.24 | 4.22 | 4.22 | 4.47 | 4.27 | 4.30 | 4.21 | 4.30 | 4.35 | 4.20 |
| Assay (%) | Hydromorphone | 102.7 | 101.0 | 99.8 | 101.3 | 102.9 | 103.8 | 101.4 | 99.7 | 100.8 | 102.7 | 102.9 |
| | Methylparaben | 103.1 | 101.0 | 100.3 | 99.9 | 99.7 | 102.2 | 101.5 | 100.1 | 99.7 | 99.0 | 100.9 |
| | Propylparaben | 101.9 | 99.1 | 99.2 | 96.7 | 91.9 | 97.2 | 98.5 | 98.0 | 95.3 | 89.2 | 94.3 |
| | EDTA | N/A | N/A | N/A | N/A | N/A | N/A | N/A | N/A | N/A | N/A | N/A |
| Degradation Products (%) | 4-Hydroxybenzoic Acid (Degradant of Parabens) | <LOQ | <LOQ | <LOQ | 0.05 | 0.06 | 0.09 | 0.05 | 0.06 | 0.10 | 0.15 | 0.27 |
| | 7-hydroperoxyl & 7-hydroxyl hydromorphone | 0.07 | 0.14 | 0.10 | 0.20 | 0.18 | 0.18 | 0.16 | 0.11 | 0.20 | 0.24 | 0.23 |

TABLE 16-continued

EDTA Free Formulation Stability 8% Oxygen Headspace

| | | Time in Weeks | | | | | | | | | |
| | | Long-Term | | | | | Accelerated | | | | |
| Test | Initial | 2 | 4 | 8 | 12 | 24 | 2 | 4 | 8 | 12 | 24 |
|---|---|---|---|---|---|---|---|---|---|---|---|
| 2,2'-bishydromorphone | 0.19 | 0.19 | 0.19 | 0.18 | 0.17 | 0.18 | 0.19 | 0.17 | 0.17 | 0.18 | 0.19 |
| Hydromorphone N-Oxide | ND | ND | ND | ND | ND | ND | ND | ND | ND | ND | ND |
| Largest Individual Unspecified Degradant | 0.05 | 0.06 | 0.06 | 0.06 | 0.19 | 0.07 | 0.05 | 0.06 | 0.05 | 0.17 | 0.07 |
| Total Degradation Products | 0.31 | 0.44 | 0.35 | 0.56 | 0.72 | 0.58 | 0.46 | 0.34 | 0.58 | 0.81 | 0.71 |

TABLE 17

EDTA Containing Formulation Stability 8% Oxygen Headspace

| | | | Time in Weeks | | | | | | | | | |
| | | | Long-Term | | | | | Accelerated | | | | |
| | Test | Initial | 2 | 4 | 8 | 12 | 24 | 2 | 4 | 8 | 12 | 24 |
|---|---|---|---|---|---|---|---|---|---|---|---|---|---|
| | Appearance | Clear colorless solution free of visible particulates | | | | | | | | | | |
| | pH | 4.06 | 4.09 | 4.05 | 4.09 | 4.17 | 4.11 | 4.12 | 4.05 | 4.16 | 4.16 | 4.10 |
| Assay (%) | Hydromorphone | 101.7 | 102.2 | 99.8 | 103.0 | 103.6 | 104.3 | 101.9 | 99.8 | 102.8 | 103.6 | 104.2 |
| | Methylparaben | 101.1 | 101.1 | 99.1 | 99.9 | 98.1 | 101.2 | 100.7 | 99.7 | 99.6 | 95.7 | 100.3 |
| | Propylparaben | 100.0 | 99.8 | 97.9 | 96.8 | 90.8 | 96.3 | 98.0 | 96.8 | 95.3 | 86.5 | 93.7 |
| | EDTA | 94.3 | 96.2 | 95.2 | 88.7 | 91.8 | 91.9 | 92.2 | 93.9 | 88.7 | 91.0 | 91.9 |
| Degradation Products (%) | 4-Hydroxybenzoic Acid (Degradant of Parabens) | <LOQ | <LOQ | <LOQ | 0.05 | 0.08 | 0.09 | 0.05 | 0.07 | 0.05 | 0.17 | 0.29 |
| | 7-hydroperoxyl & 7-hydroxyl hydromorphone | <LOQ | <LOQ | <LOQ | <LOQ | <LOQ | <LOQ | <LOQ | <LOQ | <LOQ | 0.05 | 0.05 |
| | 2,2'-bishydromorphone | <LOQ | <LOQ | <LOQ | <LOQ | <LOQ | <LOQ | <LOQ | <LOQ | <LOQ | <LOQ | <LOQ |
| | Hydromorphone N-Oxide | ND | ND | ND | ND | ND | ND | ND | ND | ND | ND | ND |
| | Largest Individual Unspecified Degradant | <LOQ | 0.05 | <LOQ | <LOQ | 0.05 | 0.06 | 0.05 | 0.05 | <LOQ | 0.22 | 0.05 |
| | Total Degradation Products | <LOQ | 0.05 | <LOQ | 0.05 | 0.24 | 0.06 | 0.05 | 0.05 | <LOQ | 0.32 | 0.11 |

In the EDTA-free formulation, 2,2'-bishydromorphone levels were high initially ((i.e., after terminal sterilization) and remained relatively constant over time. In the EDTA-free formulation, 7-hydroperoxyl & 7-hydroxyl hydromorphone levels were elevated initially (i.e., after terminal sterilization) and increased over time (i.e., during storage). In contrast, levels of 2,2'-bishydromorphone remained below the limit of quantification throughout the study in the formulation that included EDTA. Levels of 7-hydroperoxyl & 7-hydroxyl hydromorphone also were below the limit of quantification at nearly all time points and only rose above the limit after 12 weeks under accelerated storage conditions.

The results demonstrate that EDTA has at least a dual impact in that it controls the generation of degradation products such as 2,2'-bishydromorphone upon terminal sterilization and controls the generation of degradation products such as 7-hydroperoxyl & 7-hydroxyl hydromorphone during storage. Moreover, EDTA is consumed (i.e., less than 100% EDTA is retrieved) suggesting that it has antioxidant function.

Controlling the headspace during product filling to NMT 8% oxygen demonstrated lower levels of total degradation products.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A glass vial filled with a multi-dose parenteral liquid formulation, the liquid formulation comprising:
  (a) 2.0 mg/mL of hydromorphone hydrochloride;
  (b) 0.5 mg/mL of edetate disodium;
  (c) 1.8 mg/mL of methylparaben; and
  (d) 0.2 mg/mL of propylparaben;
  wherein the liquid formulation has a pH of 3.9 to 4.1,
  wherein the liquid formulation is substantially free of citrate buffer,
  wherein the liquid formulation has been terminally sterilized in a glass vial by autoclave wherein the terminal sterilization is characterized by an $F_0$ value from 10 to 20, wherein the liquid formulation has not more than 0.3% w/w of 4-hydroxybenzoic acid and not more than 0.2% w/w of 7-hydroperoxylhydromorphone and 7-hydroxylhydromorphone after terminal sterilization and storage for up to 24 weeks at 25° C.±2° C. and 60% relative humidity (RH)±5% RH, wherein the glass vial contains a 20 mL fill of the liquid formulation, and wherein the vial has a headspace comprising not more than 8% oxygen.

2. The glass vial of claim 1, wherein the liquid formulation has not more than 0.1% w/w of 4-hydroxybenzoic acid after storage for up to 24 weeks at 25° C.±2° C. and 60% relative humidity (RH)±5% RH.

3. The glass vial of claim 1, wherein the liquid formulation retains at least 95% w/w of the hydromorphone hydrocholoride and has not more than 1% w/w of 2,2'-bishydromorphone and hydromorphone N-oxide after storage at 25° C.±2° C. and 60% RH±5% RH for up to 24 weeks.

4. The glass vial of claim 1, further comprising a pH adjusting agent.

5. A method of treating a patient in need of management of pain comprising parenterally administering to the patient the liquid formulation contained in the glass vial of claim 1.

6. The method of claim 5, wherein the pain is moderate to severe pain due to surgery, cancer, soft tissue and bone trauma, biliary colic, myocardial infarction, burns, or renal colic.

7. The glass vial of claim 1, wherein the liquid formulation has not more than 0.1% w/w of 2,2'-bishydromorphone after terminal sterilization and storage for up to 12 weeks at 40° C.±2° C. and 75% RH±5% RH.

8. The glass vial of claim 1, wherein the liquid formulation has not more than 0.4% 2,2'-bishydromorphone after terminal sterilization.

* * * * *